US011529426B2

(12) United States Patent
Hasty et al.

(10) Patent No.: US 11,529,426 B2
(45) Date of Patent: Dec. 20, 2022

(54) METHODS AND COMPOSITIONS FOR TARGETING TISSUE LESIONS

(71) Applicants: Karen Hasty, Memphis, TN (US); John Stuart, Memphis, TN (US); Mary Christine Patterson, Cordova, TN (US); Hongsik Cho, Germantown, TN (US)

(72) Inventors: Karen Adcock Hasty, Memphis, TN (US); John Marvin Stuart, Memphis, TN (US); Mary Christine Patterson, Cordova, TN (US); Hongsik Cho, Germantown, TN (US)

(73) Assignees: Karen Hasty, Memphis, TN (US); John Stuart, Memphis, TN (US); Mary Christine Patterson, Cordova, TN (US); Hongsik Cho, Germantown, TN (US)

( * ) Notice: Subject to any disclaimer, the term of this patent is extended or adjusted under 35 U.S.C. 154(b) by 229 days.

(21) Appl. No.: 16/686,708

(22) Filed: Nov. 18, 2019

(65) Prior Publication Data
US 2020/0197532 A1    Jun. 25, 2020

Related U.S. Application Data

(63) Continuation of application No. PCT/US2018/033664, filed on May 21, 2018.

(60) Provisional application No. 62/509,138, filed on May 21, 2017.

(51) Int. Cl.
| | |
|---|---|
| C07K 14/78 | (2006.01) |
| C07K 16/18 | (2006.01) |
| A61K 39/395 | (2006.01) |
| A61K 47/68 | (2017.01) |
| A61K 9/51 | (2006.01) |
| C07K 16/28 | (2006.01) |
| C12N 5/0775 | (2010.01) |
| A61K 39/00 | (2006.01) |

(52) U.S. Cl.
CPC ............ *A61K 47/6898* (2017.08); *A61K 9/51* (2013.01); *A61K 39/3955* (2013.01); *C07K 14/78* (2013.01); *C07K 16/18* (2013.01); *C07K 16/2875* (2013.01); *C12N 5/0667* (2013.01); *A61K 2039/505* (2013.01); *A61K 2039/55555* (2013.01); *C07K 2317/56* (2013.01); *C07K 2317/565* (2013.01); *C07K 2317/70* (2013.01); *C07K 2319/33* (2013.01); *C07K 2319/40* (2013.01)

(58) Field of Classification Search
CPC .......... A61K 2039/505; A61K 39/3955; C07K 2317/565; C07K 2317/56; C07K 14/78; C07K 16/18; C07K 2317/70; C07K 2319/40; C07K 2319/33
See application file for complete search history.

(56) References Cited

U.S. PATENT DOCUMENTS

2005/0089578 A1*  4/2005  Werkmeister ........ C12N 5/0654
424/489

OTHER PUBLICATIONS

Bhatti et al. Characterization of physiochemical and biological properties of type II collagen targeted nanosomes. J Nanopart Res 21: 235, 2019 (13 total pages).*
Bhatti et al. Anti-inflammatory role of TPCA-1 encapsulated nanosomes in porcine chondrocytes against TNF-alpha stimulation. Inflammopharmacol 27: 1011-1019, 2019.*
Cho et al. Type II collagen antibody targets nanosomes for osteoarthritic cartilage. Conference: Orthopaedic Res Soc Annual Meeting, Poster No. 670, 2008.*
Cho et al. Theranostic immunoliposomes for osteoarthritis. Nanomed Nanotechnol Biol Med 10: 619-627, 2014.*
Cho et al. Detection of early cartilage damage using targeted nanosomes in a post-traumatic osteoarthritis mouse model. Nanomed Nanotechnol Biol Med 11: 939-946, 2015.*
Cho et al. Therapeutic efficacy of targeted TPCA-1 loaded nanosomes in post-traumatic osteoarthritis mouse model. Conference: Orthopaedic Res Soc Annual Meeting, Paper No. 0256, Mar. 2017.*
Cho et al. Noninvasive visualization of early osteoarthritic cartilage using targeted nanosomes in a destabilization of the medial meniscus mouse model. Int J Nanomed 13: 1215-1224, 2018.*
Harisa et al. An overview of nanosomes delivery mechanims: trafficking, orders, barriers, and cellular effects. Artificial Cells Nanomed Biotechnol 46(4): 669-679, 2017.*
Hasty et al. Development of TPCA-1-loaded, targeted nanosomes for inhibition of MMP-13 production of articular chondrocytes. Conference: Orthopaedic Res Soc Annual Meeting, Poster No. 0488, Mar. 2017.*
Jasin et al. Characteristics of anti-type II collagen antibody binding to articular cartilage. Arthritis Rheum 36(5): 651-659, 1993.*

(Continued)

*Primary Examiner* — Bridget E Bunner
(74) *Attorney, Agent, or Firm* — Meunier Carlin & Curfman LLC

(57) ABSTRACT

Provided are methods and compositions to target delivery of cells to a tissue lesion, thereby treating the lesion. For example, biotinylated antibodies with affinity to a lesion epitope are administered at the lesion. Reparative cells including avidin and biotin are then administered at the lesion. The reparative cells are targeted to the lesion via avidin-biotin bridges to the antibodies, with additional cells recruited to the lesion via cell-to-cell avidin-biotin bridges. In certain examples, antibody-reparative cell complexes are formed by mixing the biotinylated antibodies with the reparative cells including avidin and biotin. The complexes are then administered at the lesion. In other examples, multivalent antibodies are used to target reparative cells to the lesion, such as by binding an epitope at the lesion and an epitope present on the reparative cell. In other examples, the antibodies are chemically linked to a reparative cell or to a nanosome containing a therapeutic agent.

10 Claims, 17 Drawing Sheets
Specification includes a Sequence Listing.

(56) References Cited

OTHER PUBLICATIONS

Klareskog et al. Reactivity of monoclonal anti-type II collagen antibodies with cartilage and synovial tissue in rheumatoid arthritis and osteoarthritis. Arthritis Rheum 29(6): 730-738, 1986.*

Schnyder et al. Drug transport to brain with targeted liposomes. NeuroRx 2: 99-107, 2005.*

Terato et al. Induction of arthritis with monoclonal antibodies to collagen. J Immunol 148: 2103-2108, 1992.*

Agarwal, S., et al., "Role of NF-κB Transcription Factors in Antiinflammatory and Proinflammatory Actions of Mechanical Signals," Arthritis Rheum, 2004, vol. 50, Issue 11, PubMed PMID: 15529376, pp. 3541-3548.

Hasty, D.L., et al., "Hybridoma antibodies against protective and nonprotective antigenic determinants of a structurally defined polypeptide fragment of streptococcal M protein," Journal of Experimental Medicine, 1982, vol. 155, pp. 1010-1018.

Hollander, A.P., et al., "Damage to Type II Collagen in Aging and Osteoarthritis Starts at the Articular Surface, Originates Around Chondrocytes, and Extends into the Cartilage with Progressive Degeneration," Journal of Clinical Investigation, 1995, vol. 96, pp. 2859-2869.

Marcu, K.B., et al., "NF-κB Signaling: Multiple Angles to target OA," Current Drug Targets, vol. 11, Issue 5, PubMed PMID: 20199390, 2010, pp. 599-613.

Mengshol, J.A., et al., "Interleukin-1 induction of collagenase 3 (matrix metalloproteinase 13) gene expression in chondrocytes requires p38, c-Jun N-terminal kinase, and nuclear factor κB: differential regulation of collagenase 1 and collagenase 3," Arthritis & Rheumatism, vol. 43, No. 4, 2000, pp. 801-811.

Miller, E.J., "Isolation and characterization of a collagen from chick cartilage containing three identical α-chains," Biochemistry, vol. 10, 1971, pp. 1652-1659.

Noyori, K., et al., "Binding characteristics of antitype II collagen antibody to the surface of diseased human cartilage as a probe fortissue damage," Journal of Rheumatology, vol. 21, No. 2, 1994, pp. 293-296.

Podolin, P.L., et al., "Attenuation of Murine Collagen-Induced Arthritis by a Novel, Potent, Selective Small Molecule Inhibitor of IκB Kinase 2, TPCA-1 (2-[(Aminocarbonyl)amino]-5-(4-fluorophenyl)-3-thiophenecarboxamide), Occurs via Reduction of Proinflammatory Cytokines and Antigen-Induced T Cell Proliferation," The Journal of Pharmacology and Experimental Therapeutics, vol. 312, No. 1, 2005, pp. 373-381.

Poulet, B., et al., "Characterizing a Novel and Adjustable Noninvasive Murine Joint Loading Model," Arthritis & Rheumatism, vol. 63, No. 1, 2011, pp. 137-147.

Prockop, D.J., Repair of Tissues by Adult Stem/Progenitor Cells (MSCs): Controversies, Myths, and Changing Paradigms, Molecular Therapy. vol. 17, No. 6, 2009 pp. 939-946.

Rosloniec, E.F., et al., "Induction of Autoimmune Arthritis in HLA-DR4 (DRB1*0401) Transgenic Mice by Immunization with Human and Bovine Type II Collagen," The Journal of Immunology, vol. 160, 1998, pp. 2573-2578.

Saito, T., et al., "Transcriptional regulation of endochondral ossification by HIF-2alpha during skeletal growth and osteoarthritis development," Nature Medicine, vol. 16, No. 6, 2010, pp. 678-686.

Sandell, L.J., et al., "Articular cartilage and changes in arthritis—An introduction: Cell biology of osteoarthritis," Arthritis Research, vol. 3, No. 2, 2001, pp. 107-113.

Silver, F.H., et al., "Relationship Among Biomechanical, Biochemical and Cellular Changes Associated with Osteoarthritis," Critical Reviews in Biomedical Engineering, vol. 29, No. 4, 2001, pp. 373-391.

Stuart, J.M., et al., "Type II collagen induced arthritis in rats: Passive transfer with serum and evidence that IgG anticollagen antibodies can cause arthritis," The Journal of Experimental Medicine, vol. 155, No. 1, 1982, 16 pages.

Veronesi, F., et al., "Adipose-derived mesenchymal stem cells for cartilage tissue engineering: State-of-the-art in in vivo studies," Journal of Biomedical Materials Research, Part A, vol. 102, No. 7, 2014, pp. 2448-2466.

Wang, M., et al., "MMP13 is a critical target gene during the progression of osteoarthritis," Arthritis Research & Therapy, vol. 15, No. 1 (R5), 2013, 11 pages.

Woods, A., et al., "Human Major Histocompatibility Complex Class II-restricted T Cell Responses in Transgenic Mice," Journal of Experimental Medicine, vol. 180, Issue 1, 1994, pp. 173-181.

Zandi, E., et al., The IκB Kinase Complex (IKK) Contains Two Kinase Subunits, IKKα and IKKβ, Necessary for IκB Phosphorylation and NF-κB Activation, Cell, vol. 91, No. 2, 1997, pp. 243-252.

* cited by examiner

PREPARATION OF REAGENTS

1. BIOTINYLATE MONOCLONAL ANTIBODY TO TYPE II COLLAGEN (MabCII)

2. BIOTINYLATE REPARATIVE CELLS (RC) ADD LIMITED AMOUNT OF AVIDIN

PREPARATION OF REAGENTS

1. BIOTINYLATE MabCII

2. BIOTINYLATE REPARATIVE CELLS ADD LIMITED AOUNT OF AVIDIN

3. MIX

METHODS AND COMPOSITIONS FOR TARGETING TISSUE LESIONS

CROSS-REFERENCE TO RELATED APPLICATIONS

This application is a continuation of International Application No. PCT/US2018/033664, filed May 21, 2018, which claims priority to U.S. provisional patent application Ser. No. 62/509,138, filed May 21, 2017. The entire disclosure of the above-identified priority applications are hereby fully incorporated herein by reference.

STATEMENT OF GOVERNMENT SUPPORT

This invention was made with Government support under federal grant number AR060408 awarded by the National Institute of Health. The Government has certain rights in the invention.

REFERENCE TO A SEQUENCE LISTING

This application incorporates by reference the Sequence Listing submitted in Computer Readable Form as file 05820-005US1 SeqListing, created on Nov. 12, 2019 and containing 14 kilobytes.

TECHNICAL FIELD

The present disclosure relates generally to targeted repair of tissues lesions, and more particularly to the targeting of reparative cells or liposomes to damaged tissues, such as to damaged cartilage.

BACKGROUND

Damage to cartilage, such as in osteoarthritis (or "OA"), develops as a result of a combination of genetics, aging, trauma, obesity and possibly other as yet unidentified metabolic abnormalities. There are also certain risk factors for developing osteoarthritis, including mechanical stress and injury. Damage to the cartilage begins at the superficial cartilage layer and gradually involves deeper layers of the articular cartilage, eventually exposing subchondral bone [1,2]. Unfortunately, there are currently no established pharmacologic approaches or methodologies to prevent this progression.

More particularly, joint cartilage consists mainly of type II collagen (CII) and proteoglycans. In the earliest stages of osteoarthritis there is degradation and loss of the glycoproteins and proteoglycans on the surface of the cartilage that exposes the underlying CII fibrils [3, 4]. As the lesion enlarges, more and more CII is exposed, and further damage and loss of cells results.

With regard to mechanical stress-induced lesions, mechanical stress activates the nuclear factor-kappaB (NF-κB) pathway [16] and is thought to lead to damage of articular cartilage [17]. Activation of this pathway leads to overexpression of matrix metalloproteinases (MMPs), especially MMP-13, a proteinase that enzymatically degrades cartilage extracellular matrix (ECM) components, such as type II collagen [18]. The IkappaB kinase-2 (IKK-2) that activates NF-κB [19] could play a focal role in the NF-κB regulated production of proinflammatory molecules by mechanical stimuli [16, 18].

Regenerative medicine therapies involving reparative cells, such as stem cells or chondrocytes, hold promise in the healing of osteoarthritic lesions. One source of stem cells is adipose-derived mesenchymal stem cells (ADSCs) that have been chondrogenically differentiated in culture for use in cell-based treatments of these cartilage lesions [9]. However, it is evident that less than 1% of the cells that are delivered actually locate appropriately in the target tissues with current techniques using stem cells alone [10]. Ideally, delivery of reparative cells should be tailored to target the local lesion, as systemic delivery can have a variety of unintended and adverse consequences. Likewise, while drugs that disrupt the NF-κB signaling pathway might be useful in ameliorating the formation of mechanical stress-induced lesions, such drugs should only be delivered locally, as systemic inhibition of NF-κB would have undesirable consequences given the role of NF-κB in cell survival and its critical function in innate and adaptive immunity. Nevertheless, systemic delivery can be beneficial.

Methods and compositions are thus needed to target the delivery of reparative cells to a specific site in a subject, such as to a specific tissue or lesion within a tissue. For example, a method is needed to target reparative cells specifically to damaged cartilage, such as in osteoarthritis. Methods and compositions are also needed to slow or halt progressive tissue damage including cartilage damage that occurs in osteoarthritis. Also needed are methods and compositions for delivering drugs to a specific site, such as to a site of damaged cartilage.

SUMMARY

In certain example aspects, provided are methods of recruiting reparative cells to a lesion, such as to a cartilage osteoarthritic lesion in a subject. For example, a lesion is identified in a subject. Multiple biotinylated antibodies or antigen-binding fragments thereof are then administered at the lesion or systemically. The antibodies or fragments thereof, for example, include binding specificity to an epitope that is present at the lesion, such as type II collagen. Multiple reparative cell complexes are also administered at the identified lesion. Administration of the reparative cell complexes includes, for example, preparing multiple biotin-conjugated reparative cells by contacting the biotin-conjugated cells with an amount of avidin or variant thereof that is insufficient to saturate the conjugated biotin of the reparative cells, thereby forming the reparative cell complexes. In certain example aspects, the amount of avidin or variant thereof can saturate the conjugated biotin of the reparative cells. The subject is then contacted at the lesion with the reparative cell complexes. In certain example aspects, binding of one or more reparative cell complexes to one or more biotinylated antibodies or fragments thereof via an avidin or streptavidin bridge results in recruitment of additional reparative cell complexes to the lesion.

In certain example aspects, provided is a method of recruiting reparative cells to a lesion in a subject. The method includes, for example, preparing a first suspension that includes biotinylated antibodies or antigen-binding fragments thereof. The antibodies or fragments thereof, for example, include binding specificity to an epitope that is present at the lesion. A second suspension is also prepared, the preparation including contacting multiple biotin-conjugated reparative cells with an amount of avidin or variant thereof that is insufficient to saturate the conjugated biotin of the reparative cells, thereby forming several reparative cell complexes. In certain example aspects, the amount of avidin or variant thereof can saturate the conjugated biotin of the reparative cells. At least a portion of the first suspension is then contacted at least a portion of the second suspension, thus forming a third suspension (i.e., a mixture of the first and second suspensions). At least a portion of the third suspension is then administered to the lesion of the subject, such as by contacting the lesion with the third suspension. The third suspension, for example, can include several antibody-reparative cell complexes.

In certain example aspects, provided is a method of targeting reparative cells to a lesion. The method includes, for example, preparing a separate first suspension and a second suspension of biotinylated reparative cells. The first suspension of reparative cells is then contacted with avidin or a derivative thereof, thus allowing the avidin or derivative thereof to bind to the biotin of the reparative cells of the first suspension. The method further includes administering, at the lesion or systemically, multiple biotinylated antibodies or functional fragments thereof. In certain examples aspects, the biotinylated antibodies or functional fragments thereof can be optionally contacted with avidin. The method further includes administering, at the lesion, the first suspension of reparative cells that have been contacted with the avidin or derivative thereof and also administering, at the lesion or systemically, the second suspension of biotinylated reparative cells. In such example aspects, the administration of the first suspension of reparative cells contacted with the avidin or derivative thereof and the second suspension of biotinylated reparative cells targets the reparative cells to the lesion. Such targeting permits treatment of the lesion.

In certain example aspects, the antibodies or fragments thereof can be MabCII antibodies or fragments and the reparative cells can be adipose-derived mesenchymal stem cells. In certain example aspects, the biotinylated antibodies include an isolated antibody or antigen-binding fragment thereof that binds type II collagen. For example, the antibody or antigen-binding fragments can include the heavy and light chain CDRs of a VH/VL amino acid sequence pair set forth as SEQ ID NO: 6/14. In certain example aspects, the antibody or antigen-binding fragment can include HCDR1-HCDR2-HCDR3-LCDR1-LCDR2-LCDR3 domains set forth as SEQ ID NOs:8-10-12-16-18-20.

In further example aspects, provided is a method of recruiting reparative cells to a cartilage lesion in a subject. The method includes, for example, linking an antibody or antigen-binding fragment thereof to a reparative cell, such as by a chemical linkage. The antibody or fragment thereof, for example, includes binding specificity to an epitope that is present at the cartilage lesion. The reparative cell that is linked to the antibody or fragment thereof is then administered at a cartilage lesion of the subject. With such methods, the reparative cell that is linked to the antibody or fragment thereof can bind to the epitope at the cartilage lesion via the antibody-epitope linkage. In certain example aspects, the epitope is a type II collagen epitope. In certain example aspects, the antibody or antigen-binding fragment thereof binds type II collagen. In certain example aspects, the antibody or fragment thereof is an MabCII antibody or fragment thereof. In certain example aspects, the linked antibody or antigen-binding fragment can include the heavy and light chain CDRs of a VH/VL amino acid sequence pair set forth as SEQ ID NO: 6/14. In certain example aspects, the linked antibody or antigen-binding fragment can include HCDR1-HCDR2-HCDR3-LCDR1-LCDR2-LCDR3 domains set forth as SEQ ID NOs:8-10-12-16-18-20.

In certain example aspects, provided is a method of targeting nanosomes to a lesion in a subject, such as to a cartilage lesion. The method includes, for example, linking an antibody or fragment thereof to a nanosome, such as by a chemical linkage. The antibody or fragment thereof includes, for example, binding specificity to an epitope that is present at the lesion. The antibody-linked nanosomes are then administered at the lesion of the subject, such as at a cartilage lesion. The nanosomes, for example, can encapsulate a pharmaceutical agent, such as mediators of NF-κB (including NF-κB inhibitors such as TPCA1 or derivatives thereof). Lysis of the nanosomes at the cartilage lesion, for example, exposes the lesion to the pharmaceutical agent.

In certain example aspects, the antibody or antigen-binding fragment thereof linked to the nanosome binds type II collagen. In certain example aspects, the antibody or fragment thereof is an MabCII antibody or fragment thereof. In certain example aspects, the nanosome-linked antibody or antigen-binding fragment can include the heavy and light chain CDRs of a VH/VL amino acid sequence pair set forth as SEQ ID NO: 6/14. In certain example aspects, the linked antibody or antigen-binding fragment can include HCDR1-HCDR2-HCDR3-LCDR1-LCDR2-LCDR3 domains set forth as SEQ ID NOs:8-10-12-16-18-20.

In still further example aspects, a multivalent antibody complex can be used to recruit reparative cells to a lesion, such as to a cartilage lesion in a subject. In such methods, a lesion is identified. A first multivalent antibody complex is also prepared, the first multivalent antibody complex including a first antibody and a second antibody. The first antibody includes a binding specificity to a reparative cell surface epitope, while the second antibody includes a binding specificity to an epitope present in or near the lesion. The multivalent antibody complexes are then administered, for example, at the lesion. Further, multiple reparative cells are administered to the lesion, the reparative cells including the first reparative cell surface epitope, such as an epitope that can be recognized by the antibody complex. The administration of the reparative cells at the lesion, for example, results in recruitment of the reparative cells to the lesion. In certain example aspects, the first antibody and the second antibody include binding specificity to a type II collagen epitope, such as the same type II collagen epitope. In certain example aspects, the reparative cells are chondrogenically differentiated stem cells or chondrocytes. In certain example aspects, the first antibody has binding specificity to a transferrin epitope while the second antibody has binding specificity to a type II collagen epitope.

In certain example aspects, the methods using multivalent antibodies also include preparing a second multivalent antibody complex that includes the first antibody and a third antibody—the third antibody including binding specificity to a second reparative cell surface epitope. The second multivalent antibody complex can then be administered at the identified lesion. In certain example aspects, the first reparative cell surface epitope to which the first antibody has binding specificity is the same as the second reparative cell epitope to which the third antibody has binding specificity. In certain example aspects, the first reparative cell epitope to which the first antibody has binding specificity and the third epitope to which the third antibody has binding specificity is a transferrin epitope or other cell surface molecules on stem cells such as CD29, CD44, CD105, CD73, CD90, CD166. In certain example aspects, the reparative cells are non-chondrogenically differentiated stem cells.

In certain example aspects, provided is an isolated antibody or antigen-binding fragment thereof that binds type II collagen. The antibody or antigen-binding fragment includes, for example, the heavy and light chain CDRs of a VH/VL amino acid sequence pair set forth as SEQ ID NO: 6/14. In certain example aspects, the isolated antibody or antigen-binding fragment can include HCDR1-HCDR2-HCDR3-LCDR1-LCDR2-LCDR3 domains set forth as SEQ ID NOs:8-10-12-16-18-20. And in accordance with the methods described herein, in certain example aspects the isolated antibody or antigen-fragment thereof can include biotin. In certain example aspects, provided is an antibody-linked reparative cell or nanosome that includes (i) the anti-type II collagen antibody or antigen-binding fragment thereof and (ii) a reparative cell or nanosome.

In still further example aspects, provided are methods of treatment. The methods of treatment include, for example, any of the methods of recruiting reparative cells to a lesion described herein, such as methods of recruiting reparative cells to a cartilage lesion in a subject. The method of treatment can also include the use of antibody-linked reparative cells and nanosomes as described herein. For example, one or more therapeutic agents may be targeted to a lesion, such as a cartilage lesion, via the antibody-linked nanosomes described herein. The method of treatment can also include the use of multivalent antibody complexes as described herein. Further, the methods can use or employ the isolated antibody compositions described herein.

These and other aspects, objects, feature, and advantages of the example embodiments will become apparent to those having ordinary skill in the art upon consideration of the following detailed description of illustrated example embodiments.

BRIEF DESCRIPTION OF THE DRAWINGS

The accompanying drawings, which are incorporated in and constitute a part of this specification, illustrate certain aspects of the instant invention and, together with the description, serve to explain, without limitation, the principles of the invention. Like reference characters used therein indicate like parts throughout the several drawings.

FIG. 10A shows in vivo results, while FIG. 10B shows results after skinning and dissection. Scans of mechanically loaded (ML) mouse knee for cartilage damage and exposed type II collagen with the probe MabCII680 fluorescent dye (upper panel of FIGS. 10A-10B) and for MMP activity with the MMPSense-750 fluorescent substrate (lower panel of FIGS. 10A-10B). Left knee joints were loaded mechanically (FIGS. 10A-10B). The results indicate that there was less damaged cartilage in the group treated with TPCA-1-loaded nanosomes than the group treated with empty nanosomes or soluble TPCA-1 only. Scanning also revealed that there was lower intensity of fluorescence of MMPSense-750 in the group treated with TPCA-1-loaded nanosomes than in the control group treated with empty nanosomes or the soluble TPCA-1. This result indicates that the group treated with targeted nanosomes had lower expression of MMPs than other groups.

FIG. 12A shows a photographic image of the gross morphology of the opened pig knee cavity at 48 hr following treatment showing the cartilages of the medial femoral (MF), lateral femoral (LF), medial tibial (MT) and the lateral tibial (LT) condyles and meniscal cartilage. FIG. 12B is a photographic image of the dissected femoral condyles of the injured knee showing the surgically-induced abrasions at the arrows on the MF and LF cartilages. FIG. 12C is an optically scanned IVIS® image showing the localization of the fluorescent MabCII-targeted ADSCs (shaded areas) to the abraded cartilage areas of the femoral condyles shown in FIG. 12B, but not to the normal appearing areas of articular cartilage. As shown, within the 48 hr of treatment, MabCII-targeted ADSCs are targeted to the areas of the damaged cartilage.

DETAILED DESCRIPTION OF THE EXAMPLE EMBODIMENTS

Figure 1:
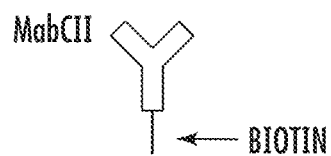
FIG. 1 is an illustration depicting the preparation of reagents for targeting reparative cell (RC) complexes to a site of damaged cartilage or osteoarthritis, in accordance with certain example embodiments.
Figure 1:
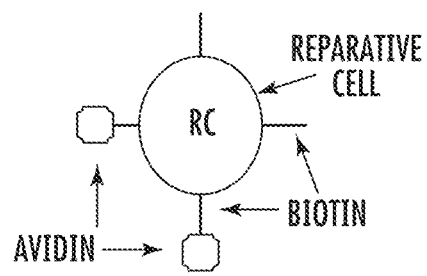

The embodiments described herein can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Summary of Terms

As used herein, the singular forms "a," "an" and "the" include plural referents unless the context clearly dictates otherwise.

Example abbreviations relevant herein include: C constant, CH constant heavy, CL constant light, CDR complementarity determining region, Fab fragment antigen binding, F(ab')2 Fab with additional amino acids, including cysteines necessary for disulfide bonds, FR framework region, Fv fragment variable, H heavy, Ig immunoglobulin, L light, scFv single chain Fv, SDR specificity determining residue, V variable, VH variable heavy, and VL variable light.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

Terms used herein, such as "example," "exemplary," or "exemplified," are not meant to show preference, but rather to explain that the aspect discussed thereafter is merely one example of the aspect presented.

Additionally, as used herein, relative terms, such as "substantially," "generally," "approximately," "about," and the like are used herein to represent an inherent degree of uncertainty that can be attributed to any quantitative comparison, value, measurement, or other representation. These terms are also utilized herein to represent the degree by which a quantitative representation can vary from a stated reference without resulting in a change in the basic function of the subject matter at issue.

"Administration" or "administering" refers to the introduction of a composition into a subject by a chosen route. For example, if the chosen route is injection, the compositions described herein can be administered by introducing the composition into a target area of a subject, such as a joint, via injection. In certain example embodiments, the compositions described herein can be injected via intra-articular injection. As used herein, "administration" or "administering" also includes systemic delivery, such as the systemic delivery of one or more of the compositions described herein.

"Animal" refers to living multi-cellular vertebrate organisms, a category that includes, for example, mammals and birds.

As used herein, an "antibody" refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. An "antibody fragment" includes Fab, Fab', F(ab')2, and Fv fragments, as well as any portion of an antibody having specificity toward a desired target epitope or epitopes. A "monoclonal antibody" is an antibody produced by a single clone of B-lymphocytes. Monoclonal antibodies can be produced by methods known to those of skill in the art, for instance by making hybrid antibody-forming cells from a fusion of myeloma cells with immune spleen cells. An "antibody" as used herein can be of any species, class, or subtype provided that such antibodies are capable of forming a linkage with a particular target ligand and can be biotinylated with a modified biotin. In certain examples, the target ligand is type II collagen.

A naturally occurring antibody (e.g., IgG) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody." Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544-546) which consists of a VH domain; and (v) an F(ab')2 fragment, a bivalent fragment comprising two Fab fragments linked by a disulfide bridge at the hinge region.

Furthermore, although the two domains of the Fv fragment are coded for by separate genes, a synthetic linker can be made that enables them to be made as a single protein chain (known as single chain Fv (scFv); Bird et al. (1988) Science 242:423-426; and Huston et al. (1988) Proc. Natl. Acad. Sci. 85:5879-5883) by recombinant methods. Such single chain antibodies, as well as dsFv, a disulfide stabilized Fv (Bera et al. (1998) J. Mol. Biol. 281:475-483), and dimeric Fvs (diabodies), that are generated by pairing different polypeptide chains (Holliger et al. (1993) Proc. Natl. Acad. Sci. 90:6444-6448), are also included.

An "antigen" is any molecule that can bind specifically with an antibody. An antigen is also a substance that antagonizes or stimulates the immune system to produce antibodies. Antigens are often foreign substances such as allergens, bacteria or viruses that invade the body.

In certain example embodiments, antibody fragments for use in this disclosure are those which are capable of cross-linking their target antigen, e.g., bivalent fragments such as $F(ab')_2$ fragments. Alternatively, an antibody fragment which does not itself cross-link its target antigen (e.g., a Fab fragment) can be used in conjunction with a secondary antibody which serves to cross-link the antibody fragment, thereby cross-linking the target antigen. Antibodies can be fragmented using conventional techniques and the fragments screened for utility in the same manner as described for whole antibodies. An antibody is further intended to include humanized monoclonal molecules that specifically bind the target antigen.

A "Complementarity Determining Region" (CDR) are amino acid sequences that together define the binding affinity and specificity of the natural Fv region of a native Ig binding site. The light and heavy chains of an Ig each have three CDRs, designated LCDR1, LCDR2, LCDR3 and HCDR1, HCDR2, HCDR3, respectively. By definition, the CDRs of the light chain are bounded by the residues at positions 24 and 34 (LCDR1), 50 and 56 (LCDR2), 89 and 97 (LCDR3); the CDRs of the heavy chain are bounded by the residues at positions 31 and 35b (HCDR1), 50 and 65 (HCDR2), 95 and 102 (HCDR3), using the numbering convention delineated by Kabat et al., (1991) Sequences of Proteins of Immunological Interest, $5^{th}$ Edition, Department of Health and Human Services, Public Health Service, National Institutes of Health, Bethesda (NIH Publication No. 91-3242).

A "Constant Region" is the portion of the antibody molecule that confers effector functions. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type.

"Epitope" refers to a site on an antigen recognized by an antibody, as determined by the specificity of the antibody amino acid sequence. Epitopes are also called antigenic determinants. For example, the epitope can be a portion of a protein that is recognized by the particular antibody. Further, the epitope can be a conformational epitope and linear epitope.

The "Framework Region" are amino acid sequences interposed between CDRs. This includes variable light and variable heavy framework regions. The framework regions serve to hold the CDRs in an appropriate orientation for antigen binding.

"Specifically binds" or "binding specificity" refers to the ability of individual antibodies to specifically immunoreact with an antigen, such as Type II collagen. This binding is a non-random binding reaction between an antibody molecule and the antigen. Binding specificity is typically determined from the reference point of the ability of the antibody to differentially bind the antigen of interest and an unrelated antigen, and therefore distinguish between two different antigens, particularly where the two antigens have unique epitopes. An antibody that specifically binds to a particular epitope is referred to as a "specific antibody."

"Chimeric antibody" refers to an antibody that includes sequences derived from two different antibodies, which typically are of different species. Most typically, chimeric antibodies include human and murine antibody fragments, generally human constant and murine variable regions.

"Humanized antibody" refers to an antibody derived from a non-human antibody, typically murine, and a human antibody which retains or substantially retains the antigen-binding properties of the parent antibody but which is less immunogenic in humans.

As used herein, the term "biotin" refers to biotin 5-[(3aS, 4S,6aR)-2-oxohexahydro-1H-thieno[3,4-d]imidazol-4-yl] pentanoic acid and any biotin derivatives and analogs thereof. Such derivatives and analogues are substances that form a complex with the biotin-binding pocket of native or modified streptavidin or avidin. Such compounds include, for example, iminobiotin, desthiobiotin, and streptavidin affinity peptides, as well as other biotin derivatives and analogues capable of binding to avidin or avidin derivatives and analogues. The term "biotinylated" is to be understood as conjugates of biotin or biotin analogues and/or derivatives with other compounds or moieties such as biomolecules. For example, a biotinylated antibody would include an antibody with a biotin molecule attached.

As used herein, "avidin" refers to a glycoprotein found in egg white and in tissues of birds, reptiles and amphibian and which has the capacity to bind to biotin with high affinity as well as to any expressed or engineered form of the avidin biotin-binding molecule, such as streptavidin, neutravidin and the like. The term includes, for example, avidin found naturally in the eggs of *Gallus gallus* (NCBI accession numbers NM-205320.1/GL45384353en) as well as the orthologues of said protein in other species. As those skilled in the art will appreciate, the avidin protein includes a tetrameric protein containing four subunits, each of which can bind to biotin. In addition to the protein avidin, at least two avidin derivatives, streptavidin and neutravidin, are capable of binding up to four biotins. As used herein, the term "avidin protein" refers to avidin and any avidin derivative capable of binding to biotin, including avidin, streptavidin and neutravidin.

"Carrier" refers to conventional pharmaceutically acceptable carriers. Remington's Pharmaceutical Sciences, by E. W. Martin, Mack Publishing Co., Easton, Pa., 19th Edition (1995), for example, describes compositions and formulations suitable for pharmaceutical delivery of the compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Example carriers include excipients or stabilizers that are nontoxic to the cell, tissue, mammal, or subject being exposed thereto at the dosages and concentrations employed. Often the pharmaceutically acceptable carrier is an aqueous pH buffered solution. Examples of pharmaceutically acceptable carriers also include, without limitation, buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween®, polyethylene glycol (PEG), and Pluronics®.

As used herein, "conjugated" means covalently attached (e.g. via a crosslinking agent). "Coupled" or "bound" means that members of a binding pair are associated, noncovalently, as through a plurality of charged interactions (ionic bonds) and non-ionic or hydrophobic interactions including VanDerWaals forces such that the bound members retain separate molecular entity.

As used herein, the term "cartilage" refers to a specialized type of connective tissue that contains chondrocytes embedded in an extracellular matrix. Several types of cartilage have been identified that differ in their histological and mechano/physical properties and include, hyaline cartilage, fibrous cartilage, and elastic cartilage. Articular cartilage that covers the apical regions of bones at the joints is composed of hyaline cartilage. The biochemical composition of cartilage differs according to type but characteristically comprises fibers, collagens and/or elastic fibers, ground-amorphous substance comprised mainly of glycosaminoglycans, proteoglycans, other proteins and water. The term "chondrocytes" as used herein, refers to cells, which are capable of producing components of cartilage tissue.

"Effective amount" or "suitable amount" or "therapeutically effective amount" refers to an amount of a substance sufficient to effect the beneficial or desired clinical or biochemical results. An effective amount can be administered one or more times. For example, an effective amount of a composition as described herein is an amount that is sufficient to facilitate repair of a lesion or slow the progression of a disease state in a lesion.

"Label" refers to a detectable compound or composition that is conjugated directly or indirectly to another molecule to facilitate detection of that molecule. Specific, non-limiting examples of labels include fluorescent tags, chemiluminescent tags, haptens, enzymatic linkages, and radioactive isotopes.

As used herein, the term "liposome" refers to vesicles or particles that possess a lipid bilayer enclosing an aqueous compartment. A "nanosome" as used herein is a nanoscale liposome. As used herein, both liposomes and nanosomes are compatible with the methods and compositions described herein. As such, the terms liposome and nanosome may at times be used interchangeably without limiting the scope of the disclosure provided herein.

The terms "lesion" as used herein refers to a circumscribed area of pathologically altered tissue, an injury or wound, or a single area of disease. The lesion can be a region in an organ, for example, that has suffered damage through injury or disease, such as a wound, ulcer, abscess, or tumor. For example, a lesion as used herein also includes an area of damaged cartilage such as in an osteoarthritic lesion. In certain examples, a lesion can be a primary lesion which is the immediate result of the pathological condition and can include, but are not limited to, cuts, abrasions, vesicles, blebs, bullae chancres, pustules, tubercles or any other such condition of the skin or a surface of the mouth, nose, anus or any other orifice of the body of a human or animal, or secondary lesions that later develop from a primary lesion and includes, but is not limited to, fissures and ulcers.

"Purified" or "isolated" molecule refers to biological or synthetic molecules that are removed from their natural environment and are isolated or separated and are free from other components with which they are naturally associated. The term "purified" does not require absolute purity; rather, it is intended as a relative term. Thus, for example, a purified or "substantially pure" protein preparation is one in which the protein referred to is more pure than the protein in its natural environment within a cell or within a production reaction chamber (as appropriate).

As used herein, the term "reparative cell" refers to any cell type that can repair or assist in the healing of a target tissue. Similarly, a reparative cell can prevent a disease in a tissue or prevent the progression of disease in a tissue. For example, the reparative cell can be a stem cell, such as an adipose-derived mesenchymal stem cell, that when administered repairs a lesion or prevents the progression of disease in a tissue.

A "subject" refers to a vertebrate. The vertebrate can be a mammal, for example, such as a human. The subject can be a human patient. A subject can be a patient suffering from or suspected of suffering from a disease or condition and can be in need of treatment or diagnosis or can be in need of monitoring for the progression of the disease or condition. The subject can also be in on a treatment therapy that needs to be monitored for efficacy. In some example embodiments, a subject includes a subject suffering from a cartilage-based disease, such as osteoarthritis.

The terms "treating" or "treatment" refer to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histidyl, is substituted for (or by) an electronegative residue, e.g., glutamyl or aspartyl.

Variant amino acid sequences can, for example, be 80, 90 or even 95 or 98% identical to the native amino acid sequence. Programs and algorithms for determining percentage identity can be found at the NCBI website.

EXAMPLE EMBODIMENTS

Provided herein are methods and compositions for targeting tissue lesions in a subject. For example, a lesion, such as a cartilage or osteoarthritic lesion, is identified in a subject. The lesion can be identified by a variety of methods known in the art, such as by medical history, x-rays, ultrasound, computed tomography, magnetic resonance imaging, and the like. The identified lesion can then be targeted according to the methods and compositions described herein. For example, a lesion, such as a cartilage lesion or osteoarthritic lesion, can be targeted by reparative cells that function to heal and repair the lesion. In other example embodiments, the lesion can be targeted by nanosomes that contain pharmaceutical agents useful in treating the lesion. These and other embodiments are described herein.

To target a lesion, the embodiments described herein rely on antibodies or functional fragments thereof that are specific to epitopes present at the site of the lesion. For example, to target a cartilage or osteoarthritic lesion, the antibodies can be reactive to a specific cartilage type known to exist at such lesions. In certain example embodiments, the targeting antibody is specific to type II collagen. In certain example embodiments, the targeting antibody is an anti-type II collagen antibody, e.g., a monoclonal antibody that binds to type II collagen and is produced by E4 antibody clone (see sequences appended). In certain example embodiments, the targeting antibody can be a chimeric or humanized antibody. In certain example embodiments, the antibody can be biotinylated. In certain example embodiments, a biotinylated targeting antibody can include avidin or variants thereof bound to the biotin. In certain example embodiments, the antibodies can include a label.

As described herein, the targeting antibodies are used to target cells, such as reparative cells, to the site of the lesion in a subject. For example, the targeting antibodies can be used to form complexes with the reparative cells. In certain example embodiments, the cells are biotinylated. For example, the targeting antibodies can be used to target biotinylated adipose-derived mesenchymal stem cells (AD-SCs) to the site of a lesion, such as to a cartilage or osteoarthritic lesion. In certain example embodiments, two or more targeting antibodies can be joined together, such as with a biotin-avidin-biotin bridge, to form a multivalent antibody complex. The multivalent antibody complex can be used to target reparative cells with type II collagen on their surface, such as chondrocytes, to an arthritic lesion where type II collagen is exposed. Additionally or alternatively, a combination of multivalent antibody complexes can be used to target non-chondrogenically differentiated reparative cells to a lesion.

In certain example embodiments, the targeting antibodies described herein can be chemically linked to cells, such as reparative cells, to form antibody-linked reparative cell complexes. In such embodiments, the antibody can directly target the reparative cell to the site of a lesion according the methods described herein. In certain example embodiments, the targeting antibodies can be chemically linked to a nanosome, thereby facilitating targeting of the nanosome (and hence the nanosome's contents) to the site of the lesion according the methods described herein. In certain example embodiments, the reparative cells or nanosomes described herein can include a label, such as a fluorescent dye, thereby permitting tracking reparative cells or nanosomes at a lesion.

With reference to FIG. 1, provided is an illustration depicting the preparation of reagents for targeting reparative cell complexes to a site of damaged cartilage or osteoarthritis, in accordance with certain example embodiments. As shown, the targeting antibodies or fragments thereof that retain antigen-binding ability are biotinylated. For example, monoclonal type II collagen antibodies (MabCII) or fragments thereof are suspended in solution and biotinylated according to methods known to those of skill in the art. Separately from the suspension of targeting antibodies, reparative cells, such as adipose-derived mesenchymal stem cells (ADSCs) that have been chondrogenically differentiated in culture for use in cell-based treatments, are suspended and biotinylated according to methods known to those of skill in the art. As shown, the biotinylation of the reparative cells (RC) results in multiple biotin molecules (or derivatives thereof) being attached to the reparative cells.

As those skilled in the art will appreciate, a variety of techniques are available for biotinylating the antibodies and reparative cells described herein. For example, biotinylation reagents and kits are available for targeting specific functional groups or residues, including primary amines, secondary amines, sulfhydryls, carboxyls, carbohydrates, phosphate groups, and the like that can serve as biotinylation targets. In certain example embodiments, biotin with different spacer arm lengths reduce steric hindrances associated with avidin or streptavidin binding and allow for efficient capturing of biotinylated proteins. Further, as those skilled in the art will appreciate, a variety of coupling or crosslinking agents can be used in well-known procedures to synthesize biotin amide analogs or biotin compounds, including carboiimide, dimaleimide, dithio-bis-nitrobenzoic acid (DTNB), N-succinimidyl-S-acetyl-thioacetate (SATA), and N-succinimidyl-3-(2-pyridyldithio) propionate (SPDP), 6-hydrazinonicotimide (HYNIC), N3 S and N2 S2. For example, biotin can be conjugated via DTPA using the bicyclic anhydride method of Hnatowich et al, Int. J Appl Radiat Isotop 33:327 (1982). In order to produce predominantly mono-biotinylated targeting ligand, the ratio of biotin to targeting ligand should be low, such as about 2:1. Further, products such as Sulfo-NHS-LC-Biotin and other EZ-Link™ systems are available from ThermoFisher Scientific (Catalog number: 21335).

For incorporation into lipid membranes of liposomes and cells, for example, a biotinylated lipid with a spacer arm such as N-Biotinyl Cap-PE 18:1 (Avanti Polar Lipids, Inc #870273) or DSPE-PEG(2000) Biotin (1,2-distearoyl-sn-glycero-3-phosphoethanolamine-N-[biotinyl(polyethylene glycol)-2000] ammonium salt) (PE-PEG-Biotin; Avanti Polar Lipids, Inc) can be mixed with liposomes and cells. (ref. 20. Loughrey, H. C., A. Ferraretto, A. M. Cannon, G. Acerbis, F. Sudati, G. Bottiroli, M. Masserini, and M. R. Soria. (1993)). Characterization of biotinylated liposomes for in vivo targeting applications. *FEBS Lett* 332, 183-188. and Corley, P., and H. C. Loughrey. (1994). Binding of biotinated-liposomes to streptavidin is influenced by liposomes composition. *Biochim Biophys Acta* 1195, 149-156. Wang T Y, Leventis R, Silvius J R. Artificially lipid-anchored proteins can elicit clustering-induced intracellular signaling events in Jurkat T-lymphocytes independent of lipid raft association. *J Biol. Chem.* 2005 Jun. 17; 280(24): 22839-46. Epub 2005 Apr. 7. PubMed PMID: 15817446.

Following the biotinylation of the reparative cells, in certain example embodiments limited amount of avidin is added to the suspension of biotin-conjugated reparative cells, thereby forming the reparative cell complexes described herein. That is, the stoichiometric amount of avidin added to the suspension of biotin-conjugated reparative cells is insufficient to saturate all of the biotin binding sites of the biotin-conjugated reparative cells. For example, based on the concentration of biotinylated reparative cells and estimated biotin sites in the suspension, the amount of avidin can be predetermined to bind to about 10%, 20%, 30%, 40%, 50%, 60%, 70%, 80%, 90, or 95% of the estimated biotin binding sites, thereby insufficiently suturing the conjugated biotin of the reparative cells.

By only partially saturating available binding sites, multiple reparative cell complexes can be formed. Each reparative cell complex includes, for example, a reparative cell, multiple conjugated biotin molecules on the reparative cell. And in certain example embodiments, a subset of the conjugated biotin molecules can be bound to avidin and a subset of the conjugated biotin molecules can have free (or open) avidin binding sites. In other example embodiments, depending on the level of biotin or variant thereof saturation, the biotin molecules conjugated to the reparative cells will have very few open free (or open) avidin or variant thereof binding sites. To prepare the reparative cell complexes for administration to a subject, the reparative cell complexes can be collected via centrifugation and washed with a buffer such as PBS to remove any excess avidin present in the suspension. The reparative cell complexes can then be suspended in a carrier, for example, that is suitable for administration to a subject.

In other example embodiments, the amount of avidin or variant thereof can saturate the conjugated biotin of the reparative cells. That is, based on the concentration of biotinylated reparative cells and estimated biotin sites in the suspension, the amount of avidin can be predetermined to bind about 100% of the estimated biotin binding sites. For example, the amount of avidin or variant thereof can be added in molar excess to the estimated amount of biotin, thereby forming avidin-saturated reparative cell complexes that can be used in accordance with the methods described herein.

In certain example embodiments, the amount of avidin or variant thereof added to the suspension of biotin-conjugated reparative cells can be predetermined to optimally interact with the biotin binding sites of the biotin-conjugated reparative cells to form the reparative cell complexes, thereby forming optimal interactions (and therefore optimal therapeutic benefit) at the lesion. For example, different amounts of avidin or variant thereof can be added to different suspensions of biotinylated reparative cells, thereby forming populations of reparative cells complexes with different ratios of avidin-biotin. The different populations can then be administered to a subject, at the lesion or systemically as described herein, to determine which ratio of avidin-biotin provides the optimal therapeutic benefit.

Figure 2:
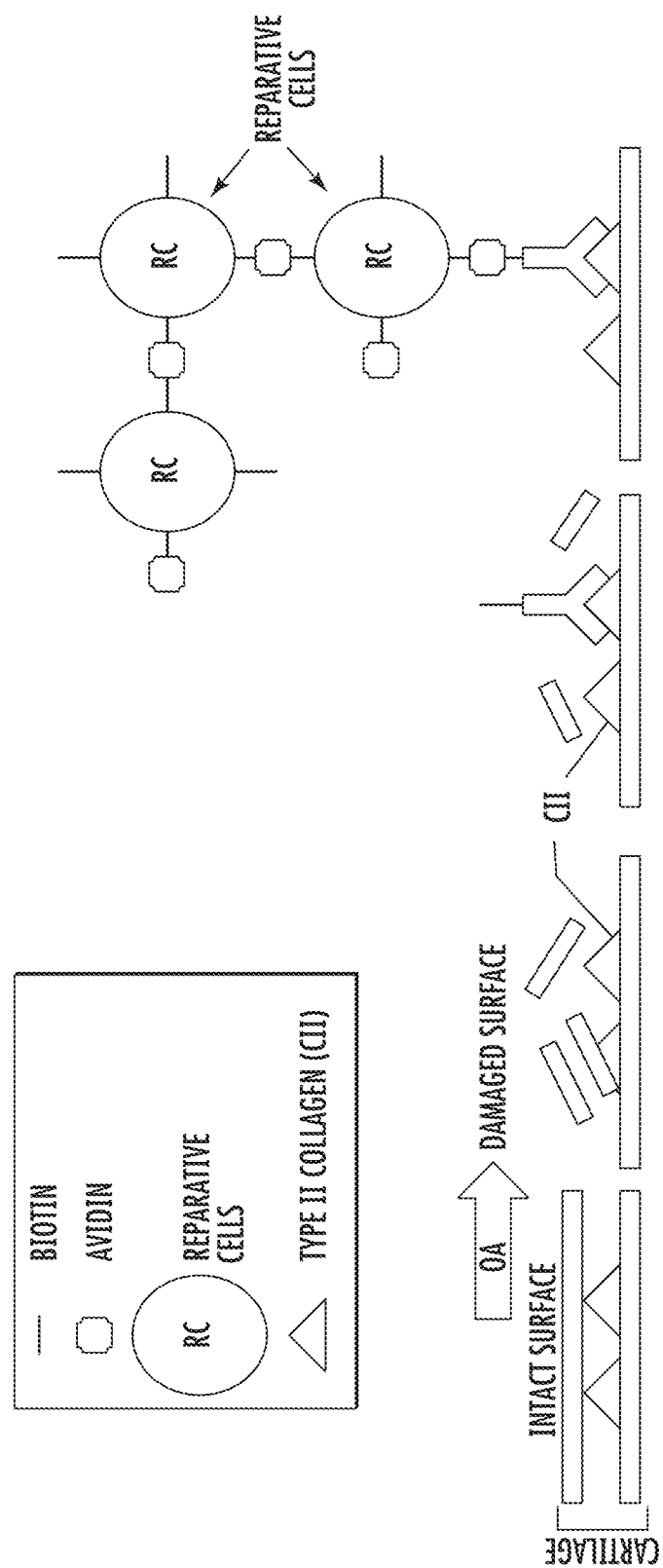
FIG. 2 is an illustration depicting the targeting of reparative cell complexes to a site of damaged cartilage or osteoarthritis (OA), in accordance with certain example embodiments. As illustrated, avidin on reparative cell complexes localizes the reparative cells (RC) to the cartilage lesion through binding to biotinylated monoclonal antibodies to type II collagen (MabCII) exposed at the cartilage lesion and propagates cell-to-cell recruitment of reparative cells at the lesion site. The biotinylated-MabCII is shown binding to type II collagen (CII), thereby initiating and propagating RC recruitment to the lesion via avidin-biotin linkages.

FIG. 2 is an illustration depicting the targeting of reparative cell complexes to a site of damaged cartilage or osteoarthritis, in accordance with certain example embodiments. Following the preparation of reagents described herein (see FIG. 1), for example, the biotinylated targeting antibodies can be administered to the site of damaged cartilage or osteoarthritis (FIG. 2). For example, a suspension of the targeting antibodies is injected at the site of the lesion. If the lesion is a cartilage or osteoarthritic lesion in a knee joint, for example, the suspension of the targeting antibodies is injected into the knee into the proximity of the lesion. In other example embodiments the biotinylated antibodies can be delivered systemically.

In addition to the targeting antibodies, a suspension of reparative cell complexes is administered at the lesion site (FIG. 2). For example, if the lesion is a cartilage or osteoarthritic lesion in a knee joint, the suspension of reparative cell complexes can be injected into the synovial cavity of the knee into the proximity of the lesion (i.e., proximate to the site of targeting antibody injection). In certain example embodiments, the suspension of reparative cell complexes is administered at the same time or before the administration of the targeting antibodies. Alternatively, the suspension of reparative cell complexes can be administered after the administration of the targeting antibodies. For example, the suspension of reparative cell complexes can be administered at 1, 2, 3, 4, 5, 6, 7, 8, 12, 16, or about 24 hours following the administration of the targeting antibodies at the site of the lesion.

Without wishing to be bound by any particular theory, and as illustrated in FIG. 2, it is believed that administration of the targeting antibodies and the reparative cell complexes to the site of the lesion results in recruitment of reparative cells to the lesion, which in turn results in repair of the lesion. For example, when biotinylated targeting antibodies to type II collagen are injected at the site of the lesion, the antibodies bind the exposed type II collagen at the lesion. Thereafter, when the reparative cell complexes come into contact with the bound antibodies, the avidin of the avidin-bound biotin sites of the reparative cells forms an avidin-biotin bridge between the biotin bound to the antibody and the biotin conjugated to the reparative cell. In this way, the bridge links the reparative cell complex to the antibody and hence localizes the reparative cell complexes to the site of lesion (FIG. 2).

When additional reparative cell complexes come in to contact with the reparative cell complex bridged to the antibody, these additional reparative cell complexes are believed to form avidin-biotin linkages with the reparative cell complex bridged to the antibody, thus facilitating further recruitment of reparative cell complexes to the lesion (FIG. 2). And, through propagation of additional avidin-biotin linkages among multiple reparative cell complexes, multiple reparative cells can be recruited to the site of the lesion, thereby forming network of reparative cells as the site of the lesion. Such propagation of reparative cell complexes to the lesion is, for example, believed to result in a targeted repair of the lesion (FIG. 2).

Figure 3:
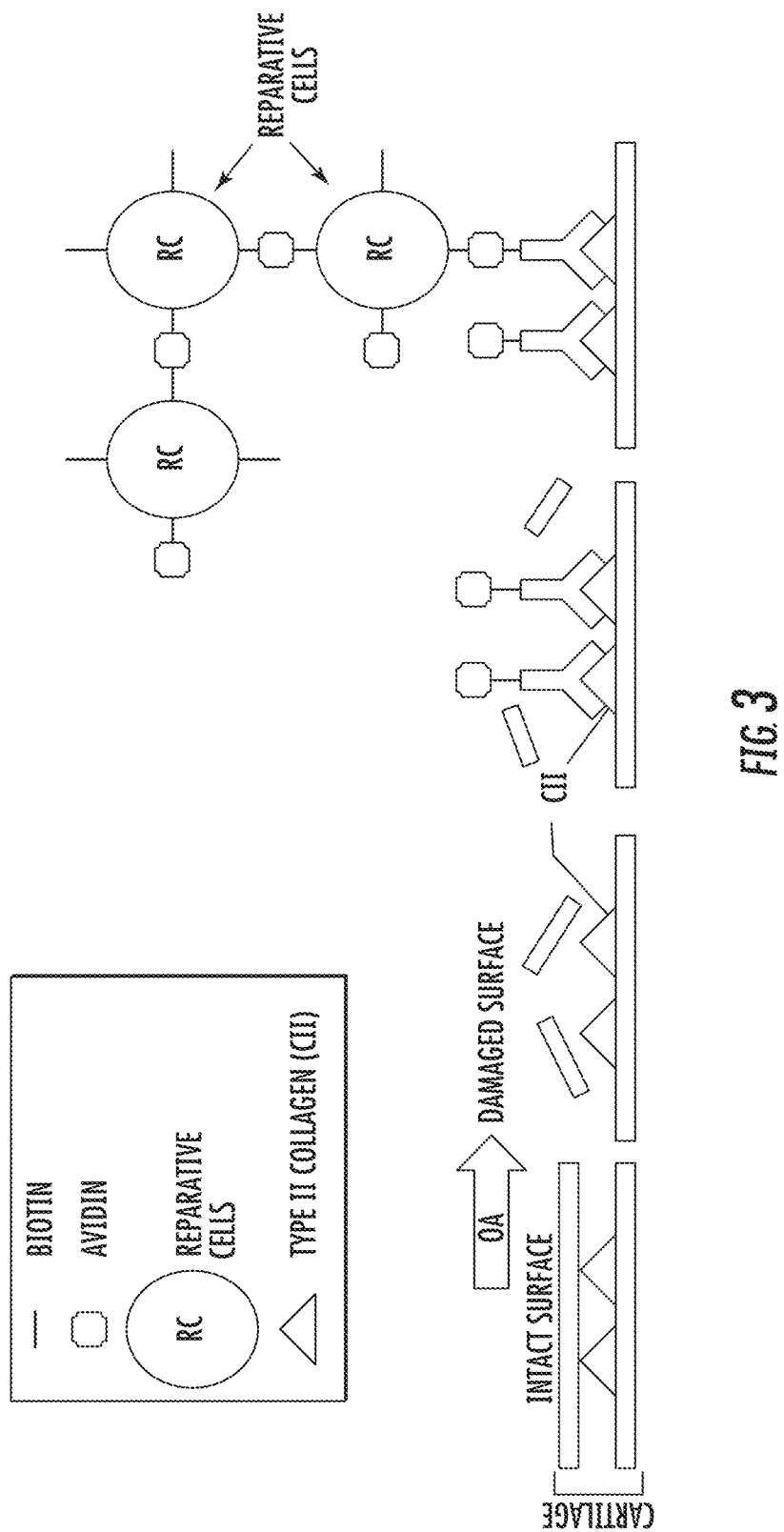
FIG. 3 is an illustration depicting the targeting of reparative cell complexes to a site of damaged cartilage or osteoarthritis (OA) via avidin/biotin-linked antibodies, in accordance with certain example embodiments. As illustrated, the reparative cell complexes localize to the cartilage lesion via the avidin/biotin-linked antibodies bound at the cartilage lesion and propagate through cell-to-cell recruitment of reparative cells (RC) at the lesion. The avidin/biotin-linked antibodies are shown binding to type II collagen, thereby initiating and propagating RC recruitment to the lesion via avidin-biotin linkages.

With reference to FIG. 3, provided is an illustration depicting the targeting of reparative cell complexes to a site of damaged cartilage or osteoarthritis, as described herein, but also via avidin/biotin-linked antibodies, in accordance with certain example embodiments. For example, following the biotinylation of the targeting antibodies as described herein, the antibody suspension is mixed with avidin to form an antibody-biotin-avidin targeting complex. In certain example embodiments, the amount of avidin mixed with the antibody suspension fully saturates the amount of biotin. That is, enough avidin is added to the targeting antibody suspension so that each biotin molecule is expected to be bound by the avidin. In other examples embodiments, the amount of avidin can be adjusted to only partially saturate the biotinylated targeting antibodies. For example, the amount of avidin can be adjusted such that only 10%, 20%, 30%, 40%, 50%, 60%, 70%, 80%, 90, or 95% of the biotinylated-antibodies are bound to avidin. In certain example embodiments, following the addition of avidin to the biotinylated antibody suspension, the antibody-biotin-avidin targeting complexes can be collected via centrifugation and washed with a buffer such as PBS to remove any excess avidin present in the suspension. The antibody-biotin-avidin targeting complexes can then be suspended in a carrier, for example, that is suitable for administration to a subject.

When avidin is added to form antibody-biotin-avidin targeting complex as described herein, the administration of the antibody-biotin-avidin complexes results in binding of the antibody-biotin-avidin targeting complex to the target protein (FIG. 3). For example, use of type II collagen antibodies results in binding of the antibody-biotin-avidin targeting complex to type II collagen (FIG. 3). Following the administration of the reparative cell complexes as described herein, it is believed that the avidin of the antibody-biotin-avidin targeting complexes forms a bridge with the reparative cell complexes, thus targeting the reparative cell complexes to the site of the lesion (FIG. 3). Additional reparative cell complexes can then be recruited to the lesion as described herein, thus propagating a network of reparative cells at the lesion (FIG. 3).

In certain example embodiments, a first and second suspension of biotinylated reparative cells can be prepared. For example, a single suspension of reparative cells can be biotinylated as described herein, and the resultant suspension of biotinylated cells then divided into a first and second suspension of biotinylated reparative cells. Additionally or alternatively, the first and second suspension of biotinylated reparative cells can be prepared separately. In such example embodiments, the first suspension of biotinylated reparative cells be saturated with avidin or a variant thereof. For example, an amount of avidin or variant thereof can be added in a molar excess to the estimated amount of biotin, thereby saturating the biotin conjugated to the reparative cells. The suspension of avidin-saturated cells can then be washed, for example, in a suitable buffer (e.g., PBS, TBS, etc.), to remove any excess avidin or derivative thereof. Following the local or systemic administration of biotinylated antibodies, such as MabCII antibodies, to a lesion as described herein, the first and second suspension can be administered at the lesion, thereby permitting the first and second suspension to contact each other. Additionally or alternatively, the first and second suspension can be mixed together before the administration at the lesion.

In such example embodiments, the avidin-saturated biotinylated reparative cells (from the first suspension) can serve as nucleation sites for recruitment of the non-avidin-conjugated biotinylated reparative cells (from the second suspension). That is, the avidin-saturated biotinylated reparative cells of the first suspension can bind to the biotinylated reparative cells of the second suspension when the first and second suspension are brought into contact with each other, via a biotin-avidin-biotin bridge. That contact, for example, can occur upon the co-administration of the first and second suspensions at the lesion. Additionally, or alternatively, the contact that facilitates binding between the avidin-saturated biotinylated reparative cells of the first suspension and the biotinylated reparative cells of the second suspension can occur by mixing the first and second suspension before administration. The mixture can then be administered at the lesion.

Without wishing to be bound by any particular theory, it is believed that administration of the targeting antibodies and the first and second suspension results in the recruitment of reparative cells to the lesion, which in turn results in repair of the lesion. For example, when biotinylated targeting antibodies to type II collagen are injected at the site of the lesion (or systemically delivered), the antibodies bind the exposed type II collagen at the lesion. Thereafter, when the reparative cells of the first and second suspension come into contact with the bound antibodies, the avidin of the avidin-bound biotin sites of the reparative cells forms an avidin-biotin bridge between the biotin bound to the antibody and the biotin conjugated to the reparative cell. In this way, the bridge links the reparative cells to the antibody and hence localizes the reparative cell complexes to the site of lesion (See, e.g., FIG. 2).

As those skilled in the art will appreciate based on this disclosure, the biotinylated antibodies can, in certain example embodiments, be partially or fully saturated with avidin or variant thereof before administration of the antibodies. For example, when the reparative cells of the first and second suspension come into contact with the bound antibodies, the biotin of the bound biotin sites of the reparative cells forms an avidin-biotin bridge between the avidin bound to the antibody and the biotin conjugated to the reparative cell (See, e.g., FIG. 3). Further, while in certain example embodiments full saturation of the biotinylated reparative cells of the first suspension may be preferred, in certain example embodiments the amount of avidin or variant thereof added to the reparative cells of the first suspension may be optimized to provide the maximum therapeutic effect. In such example embodiments, the amount of avidin or variant thereof may only partially saturate the biotinylated reparative cells as described herein. Additionally or alternatively, the level of biotinylated antibody saturation with avidin can also be optimized as described herein.

Figure 4A:
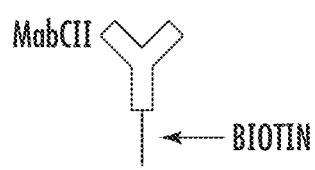
FIG. 4A is an illustration depicting the preparation of reagents for targeting antibody-reparative cell complexes to a site of damaged cartilage or osteoarthritis, in accordance with certain example embodiments. As shown, antibodies are joined to reparative cells (RC) via avidin-biotin linkage to form an antibody-reparative cell complex.
Figure 4A:
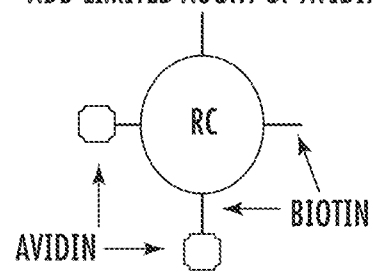
Figure 4A:
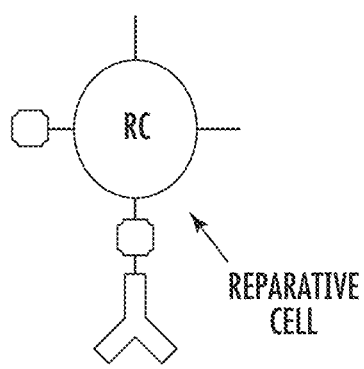

FIG. 4A is an illustration showing the preparation of reagents for targeting antibody-reparative cell complexes to a site of damaged cartilage or osteoarthritis, in accordance with certain example embodiments. As shown, the biotinylated targeting antibodies can be prepared as described herein, as are the reparative cell complexes. But before either the biotinylated targeting antibodies or the reparative cell complexes are administered to a subject, these reagents can be mixed together. As shown in FIG. 4A, the mixing of the biotinylated targeting antibodies and the reparative cell complexes results in an antibody-reparative cell complex, the antibody being attached to the complex via a biotin-avidin linkage, as shown (FIG. 4A). In certain example embodiments, following the formation of the antibody-reparative cell complexes, the complexes are collected via centrifugation and washed with a buffer such as PBS, TBS, or other suitable wash buffer. The antibody-reparative cell complexes can then be suspended in a carrier, for example, that is suitable for administration to a subject.

Figure 4B:
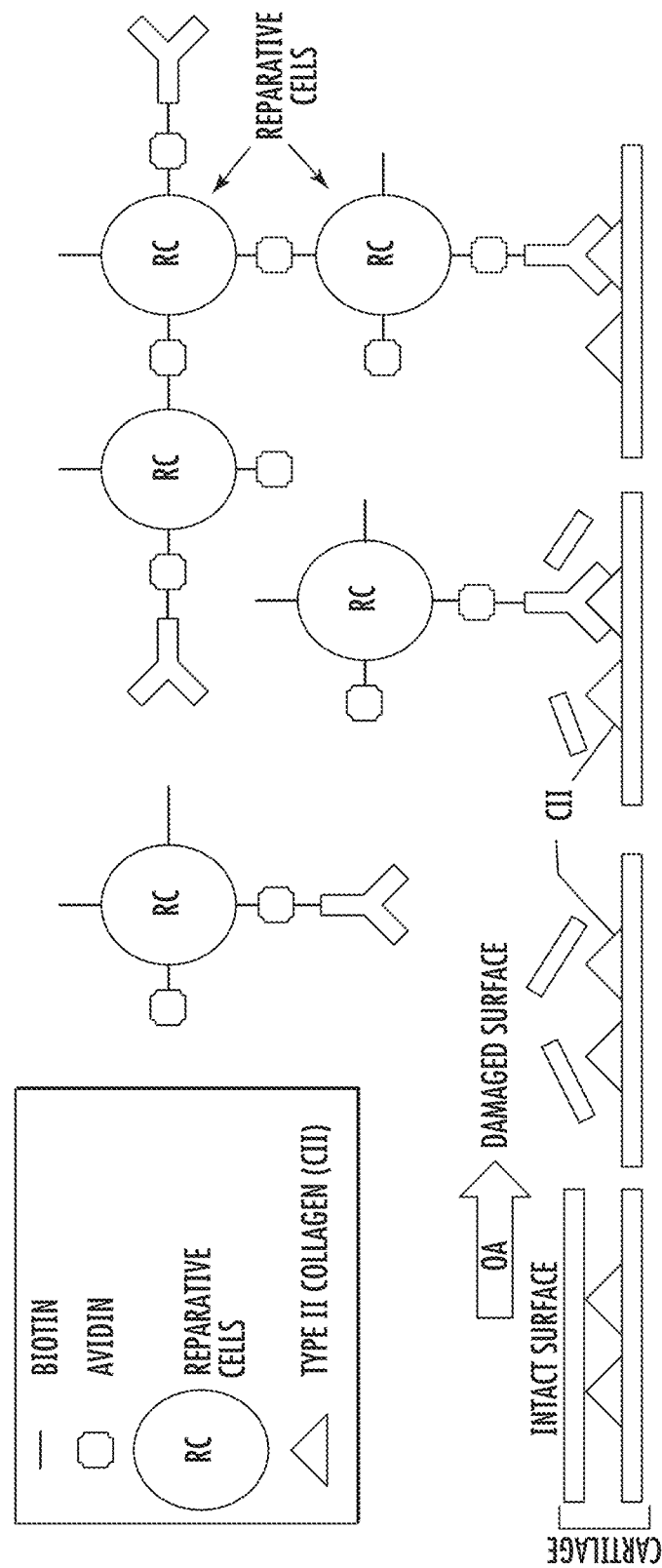
FIG. 4B is an illustration depicting the targeting of antibody-reparative cell complexes to the site of damaged cartilage or osteoarthritis (OA), in accordance with certain example embodiments. As illustrated, the antibodies on the reparative cell complexes localize the reparative cell complexes to the cartilage lesion, and the reparative cell complexes then propagate cell-to-cell recruitment of reparative cells at the lesion. The antibody of the antibody-reparative cell complex is shown binding to type II collagen (CII), thereby targeting reparative cells (RC) to the lesion.

FIG. 4B is an illustration depicting the targeting of antibody-reparative cell complexes to the site of damaged cartilage or osteoarthritis, in accordance with certain example embodiments (such as by using the reagents described in FIG. 4B). For example, following the formation of the antibody-reparative cell complexes (FIG. 4B), the antibody-reparative cell complexes can be administered to a subject at the site of a lesion as described herein, such as by injection of the antibody-reparative cell complexes to a site of osteoarthritis. Administration at the site of the lesion, for example, allows the antibody-reparative cell complexes to come in to contact with the target tissue of the lesion.

Without wishing to be bound by any particular theory, it is believed that the antibodies on the reparative cell complexes localize the reparative cell complexes to the lesion. If the antibody is specific to type II collagen, for example, the antibody is believed to target the antibody-reparative cell complex to type II collagen via the binding of the antibody of the complex to the type II collagen at the lesion. As shown in FIG. 4B, for example, an MabCII antibody portion of the antibody-reparative cell complex localizes the reparative cell complexes to a cartilage lesion via binding of the antibody to the cartilage. That is, the MabCII antibody portion of the antibody-reparative cell complex binds the target protein, i.e., type II cartilage (FIG. 4B). Additional reparative cell complexes can then be recruited to the lesion as described herein, thus propagating a network of reparative cells at the lesion (FIG. 4B).

In certain example embodiments, multivalent antibody complexes can be used to target reparative cells to a site of a lesion. For example, multivalent antibody complexes can be used to target chondrocytes, chondrogenically differentiated stem cells, or non-chondrogenically differentiated stem cells to an osteoarthritic lesion. In certain example embodiments, one antibody of the multivalent antibody complexes can bind an epitope on a reparative cell while the other antibody binds to an epitope that is present at the lesion. The epitopes can be any epitopes that, when used in accordance with the methods described herein, target the reparative cells to the lesion.

With regard to chondrocytes and chondrogenically differentiated stems cells, reparative cell-to-cell binding and recruitment to the osteoarthritic lesion site can occur through multivalent antibody binding of type II collagen on the cell surface of the reparative cells (or via the binding to other antigens on the cell surface). For example, MabCII antibodies or functional fragments thereof may bind collagen on the surface of reparative cells or a peptide pf collagen that is bound to the cell. For undifferentiated stems cells—i.e., cells that do no express collagen on their surface—the reparative cell-to-cell binding and recruitment to the lesion site can occur through multivalent antibody binding to antigens present on the cell surface, such as transferrin or other cell surface molecules on stem cells such as CD29, CD44, CD105, CD73, CD90, CD166, or combinations thereof.

Figure 5A:
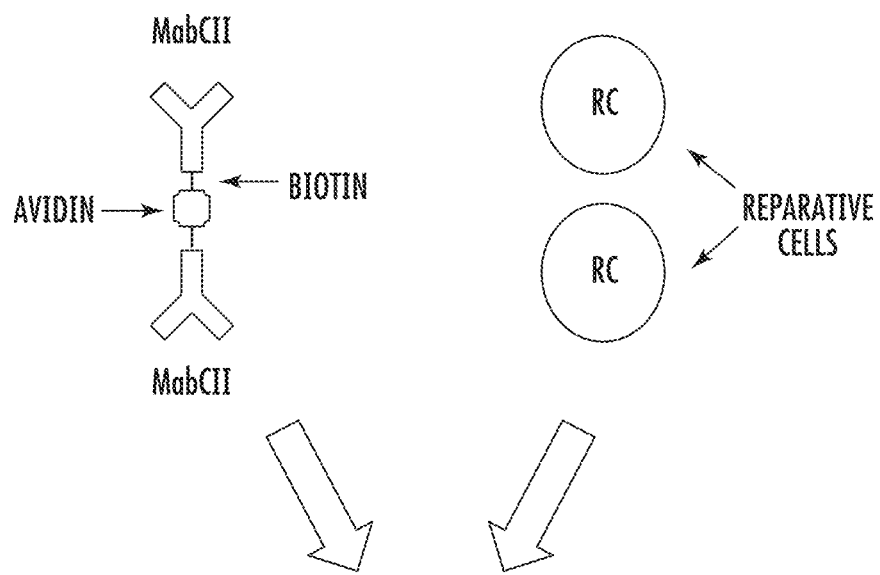
FIG. 5A is an illustration depicting the preparation of multivalent antibody complexes for targeting reparative cells to a site of damaged cartilage or osteoarthritis, in accordance with certain example embodiments. For example, the multivalent MabCIIs can bind to type II collagen at the lesion and to surface epitopes (such as type II collagen or a collagen peptide) of reparative cells (RC), the reparative cells being chondrocytes or chondrogenically differentiated reparative cells, for example.

In accordance with such embodiments, FIG. 5A is an illustration depicting the preparation of multivalent antibody complexes for targeting reparative cells to a site of damaged cartilage or osteoarthritis. As shown, multivalent antibody complexes can be prepared by linking antibodies, such as MabCII antibodies or functional fragments thereof, to each other. For example, the multivalent antibody complex can be formed by joining two or more antibodies together with a biotin-avidin-biotin bridge is illustrated in FIG. 5A. With such a multivalent antibody complex configuration—and with the use of the MabCII antibody, for example—the complex can be used to target chondrocytes or chondrogenically differentiated stem cells that synthesize and assemble type II collagen on the cell surface. For example, the two MabCII antibodies or portions thereof can be linked together as shown (FIG. 5A) to form the multivalent antibody complex. In certain example embodiments, the multivalent antibody complexes and the reparative cells can be mixed together before administration to a subject. Additionally or alternatively, the multivalent antibody complexes and the reparative cells can be administered separately before mixing these reagents.

Figure 5B:
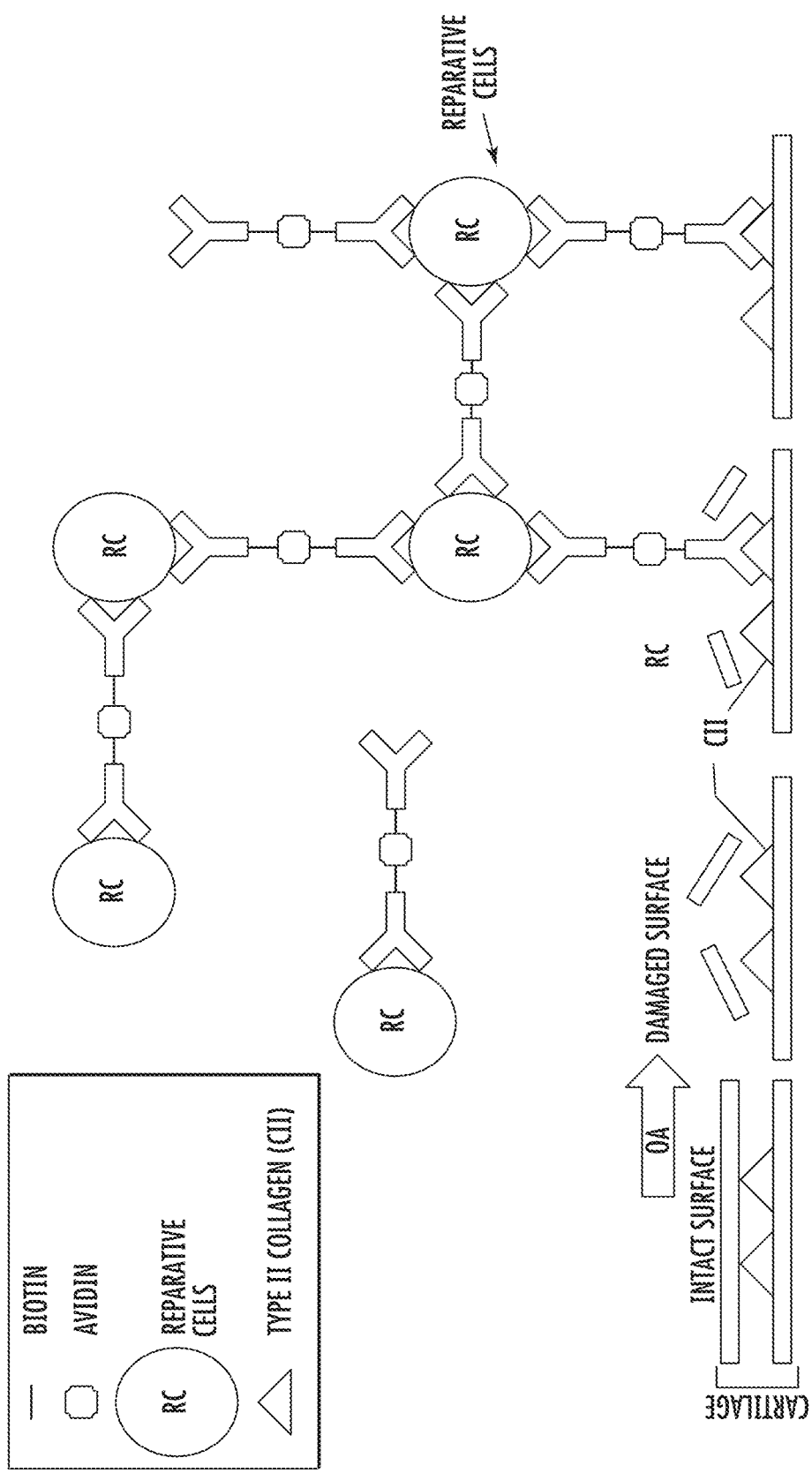
FIG. 5B is an illustration depicting the targeting of reparative cells to the site of a lesion via multivalent antibody complexes described in FIG. 5A, in accordance with certain example embodiments. As illustrated, the multivalent antibody complex, by binding both to the lesion and to the reparative cell, serves to target reparative cells to the lesion. Further, by linking one reparative cell to another reparative cell, the multivalent antibody complex recruits reparative cells to the lesion through binding to type II collagen (CII).

Using the multivalent antibody complexes prepared as described in FIG. 5A, for example, FIG. 5B provides an illustration depicting the targeting of reparative cells to the site of a lesion via the multivalent antibody complexes, in accordance with certain example embodiments. As shown, contacting the multivalent antibody complexes and the reparative cells results in binding of the multivalent antibody complexes and the reparative cells (FIG. 5B). Without wishing to be bound by any particular theory, it is believed that this binding facilitates both targeting of the reparative cells to the lesion and the recruitment of additional reparative cells to the lesion site (FIG. 5B). For example, with MabCII antibodies, the multivalent antibody complexes bind both the type II cartilage at the lesion and the type II cartilage expressed on the differentiated reparative cell. The reparative cells can then be localized to an osteoarthritic lesion through the binding of the multivalent antibody complex to the damaged cartilage and the concomitant binding of the multivalent antibody complex to the reparative cell (FIG. 5B). The recruitment of reparative cells linked together by the multivalent MabCII is then believed to occur as shown (FIG. 5B), thereby forming an aggregate of reparative cells at the lesion.

While FIG. 5A and FIG. 5B show two MabCII antibodies, it is to be understood that, in certain example embodiments, one antibody of the antibody pair shown can bind to any epitope present on the reparative cell, while the other antibody can bind to any epitope present at the lesion, such as type II cartilage. Additionally or alternatively, while the methods illustrated in FIG. 5A and FIG. 5B can be preferably used for recruiting chondrocytes or chondrogenically differentiated stem cells to a lesion (with the use of MabCII antibodies, for example), the methods described in FIG. 5C and FIG. 5D below—which make use of cell surface antigens on the reparative cell surface—can be used to target undifferentiated stem cells to the lesion.

Figure 5C:
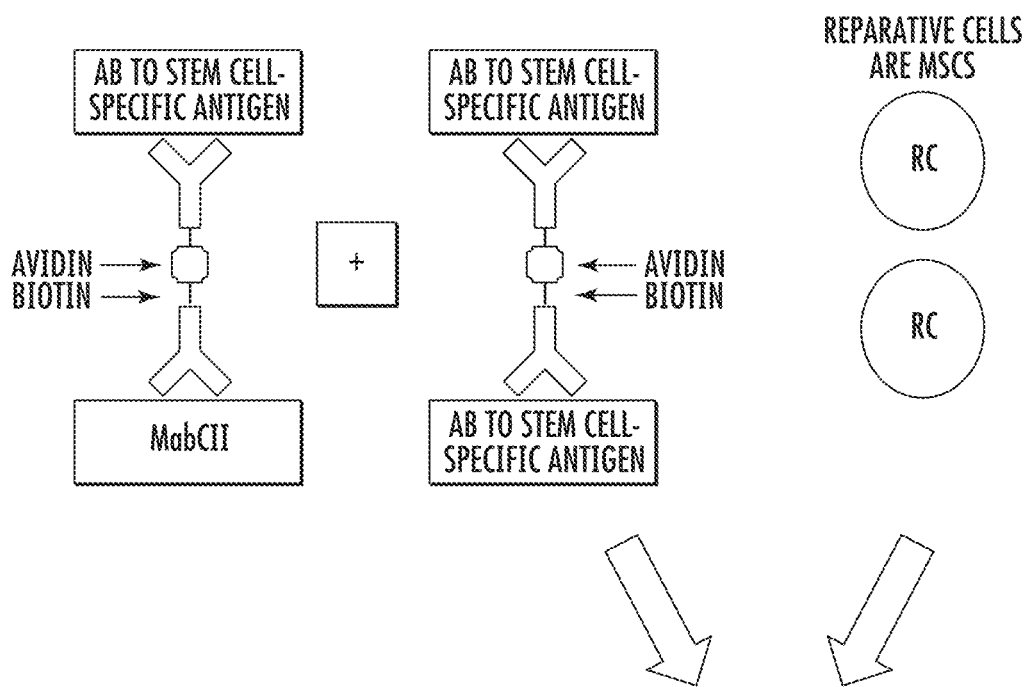
FIG. 5C is an illustration depicting the preparation of reagents for targeting non-chondrogenically differentiated reparative cells to a lesion, in accordance with certain example embodiments. As illustrated, multivalent antibody complexes are prepared that have binding specificity to lesion-site collagen, for example—and to the reparative cells (RC). Additional multivalent antibody complexes can also be prepared that have antibodies to stem cell-specific antigens, as shown.

With regard to targeting undifferentiated reparative cells to a lesion, such as undifferentiated mesenchymal stem cells (MSCs), a similar method can be employed to target the undifferentiated reparative cells to the lesion. FIG. 5C, for example, provides an illustration depicting the preparation of reagents for targeting non-chondrogenically differentiated reparative cells to a lesion, in accordance with certain example embodiments. As illustrated, multivalent antibody complexes can be prepared that have binding specificity to lesion-site collagen, for example, and also to the reparative cells. For example, a hybrid multivalent antibody complex can be made through an avidin linkage of lesion-targeting biotinylated MabCII to a different biotinylated antibody component specific for a mesenchymal stem cell (MSC) surface antigen, as described by (1) Dominici, M., et al., Minimal criteria for defining multipotent mesenchymal stromal cells. The International Society for Cellular Therapy position statement. *Cytotherapy*, 2006. 8(4): p. 315-7 and (2) Bourin, P., et al., Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT). *Cytotherapy*, 2013, 15(6): p. 641-648.

Then, to promote cell-to-cell recruitment of other MSCs to the MSCs initially targeted to the OA lesion with the first hybrid multivalent antibody complex, a second multivalent antibody complex can be used that is made by biotinylation and avidin linkage of antibodies specifically recognizing a mesenchymal stem cell antigen (FIG. 5C). For example, both types of multivalent antibody complexes can then be combined and mixed with reparative cells, such as mesenchymal stem cells (FIG. 5C). The mixture can then administered at the site of at a lesion, such as via intra-articular injection into a damaged joint. Additionally or alternatively, the mixing of the multivalent antibody complexes and the reparative cells can occur at the site of the lesion.

Figure 5D:
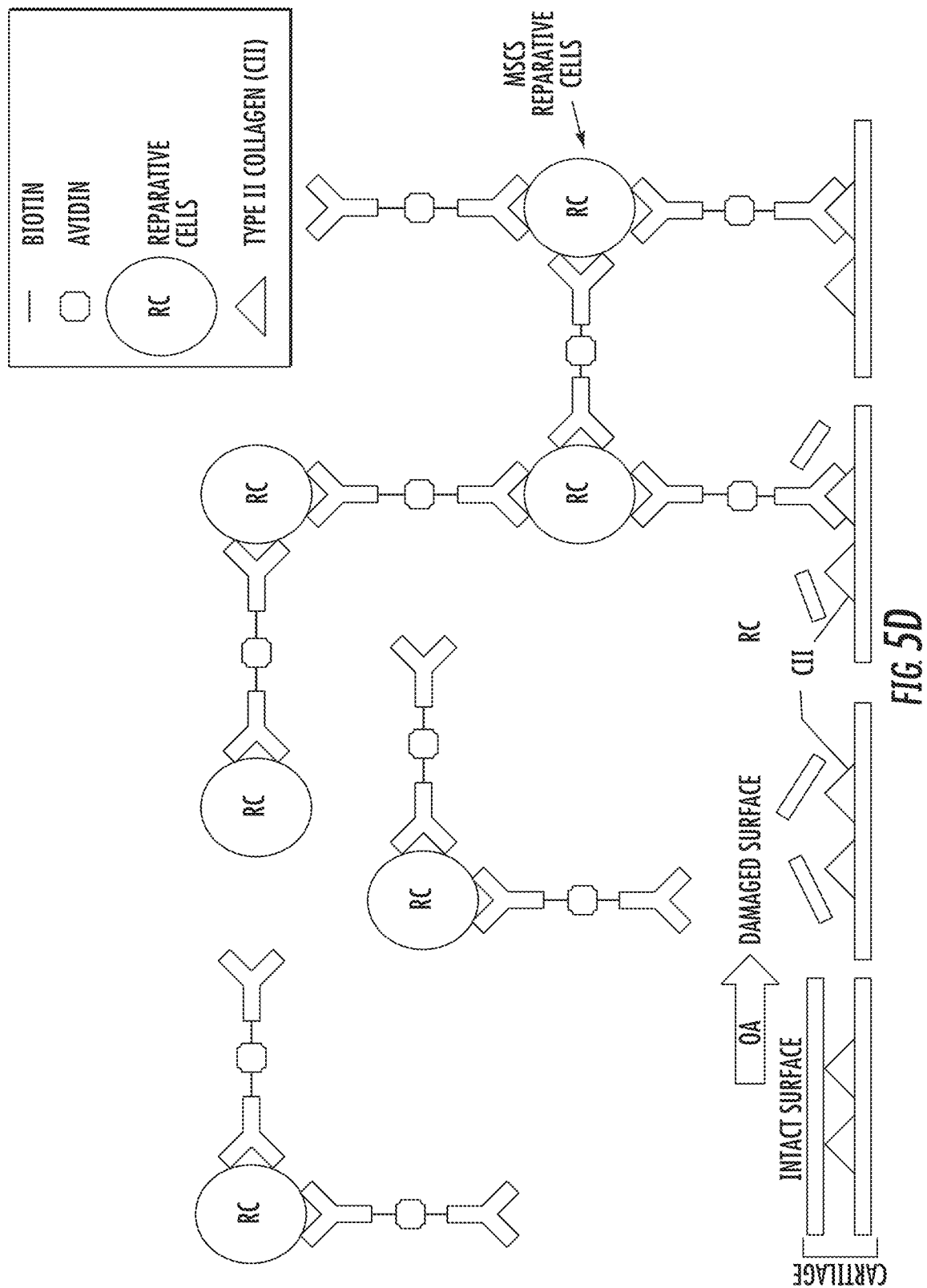
FIG. 5D is an illustration depicting the targeting of non-chondrogenically differentiated reparative cells to the site of a lesion via multivalent antibody complexes, in accordance with certain example embodiments. As illustrated, and following the preparation of reagents as described in FIG. 5C, a first multivalent antibody complex targets reparative cells (RC) to the site of the lesion, such as to type II collagen (CII) at the lesion. An additional multivalent antibody complex then recruits additional reparative cells to the lesion.

Using the multivalent antibody complexes prepared as described in FIG. 5C, for example, FIG. 5D provides an illustration depicting the targeting of non-chondrogenically differentiated reparative cells to the site of a lesion via multivalent antibody complexes, in accordance with certain example embodiments. As illustrated, a first multivalent antibody complex targets reparative cells to the site of the lesion, such as to collagen at the lesion. An additional multivalent antibody complex then recruits additional reparative cells to the lesion. Without wishing to be bound by any particular theory, it is believed that multivalent antibody complexes facilitate the targeting of undifferentiated mesenchymal stem cells to a cartilage lesion and the recruitment of more MSCs to that site by linkages of multivalent antibody complexes specific only for stem cell antigens.

In certain example embodiments, and as those skilled in the art will appreciate, following the formation of the mixture of multivalent antibody complexes and reparative cells as described herein, the mixture is subjected to centrifugation and the bound multivalent antibody complexes/reparative cells can be collected. The collected multivalent antibody complexes/reparative cells can then be washed with a buffer such as PBS or TBS (or other suitable was buffer). The multivalent antibody complexes/reparative cells can then be suspended in a carrier, for example, that is suitable for administration to a subject as described herein.

Figure 6A:
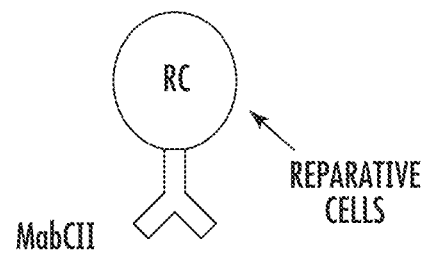
FIG. 6A is an illustration depicting the preparation of reagents for targeting an antibody-linked reparative cell to damaged cartilage or an osteoarthritic lesion, in accordance with certain example embodiments. As shown, an antibody to type II collagen, for example, is linked directly to the reparative cell (RC).

FIG. 6A is an illustration depicting the preparation of reagents for targeting an antibody-linked reparative cell to a damaged cartilage or osteoarthritis, in accordance with certain example embodiments. As shown, in this example embodiment targeting antibodies can be chemically linked to the reparative cells, thereby forming a direct chemical linkage with the cell. The targeting antibodies, for example, can be any antibody that is specific to a protein known to be present at a lesion. For example, to target cartilage and/or osteoarthritic lesions, type II monoclonal antibodies can be linked to reparative cells. The attachment of the antibody to the reparative cell then forms an antibody-linked reparative cell complex as shown in FIG. 6A.

As those skilled in the art will appreciate, a variety of methods are known for chemically linking an antibody to a cell such as a reparative cell. For example, a population of reparative cells can be suspended in a solution with a heterobifunctional cross-linking agent, succinimidyl-4-(N-maleimidomethylcyclohexane)-1-carboxylate (SMCC) which covalently links to the primary amines of the antibody. The antibody conjugate can then be incubated with reparative cells previously treated with dithiothreitol, washed and used for injection. See, e.g., Eisenthal A, Rosenberg S A. Cross-linking of anti-B16 melanoma monoclonal antibodies to lymphokine activated killer (LAK) cells: possible role in the therapy of B16 melanoma. Clin Exp Metastasis. 1988 September-October; 6(5):387-400. PMID: 3378376; Christiaansen J E, Gallardo D, Burnside S S, Nelson A A, Sears D W. Rapid covalent coupling of proteins to cell surfaces: immunological characterization of viable protein-cell conjugates. J Immunol Methods. 1984 Nov. 30; 74(2):229-39. PMID: 6094668, each of which are hereby expressly incorporated herein in their entirety. Following the conjugation of the antibodies to the reparative cells to form antibody-linked reparative cell complexes, the suspension of antibody-reparative cell complexes can be collected via centrifugation and washed with a buffer such as PBS. The antibody-linked reparative cell complexes can then be suspended in a carrier, for example, that is suitable for administration to a subject.

Figure 6B:
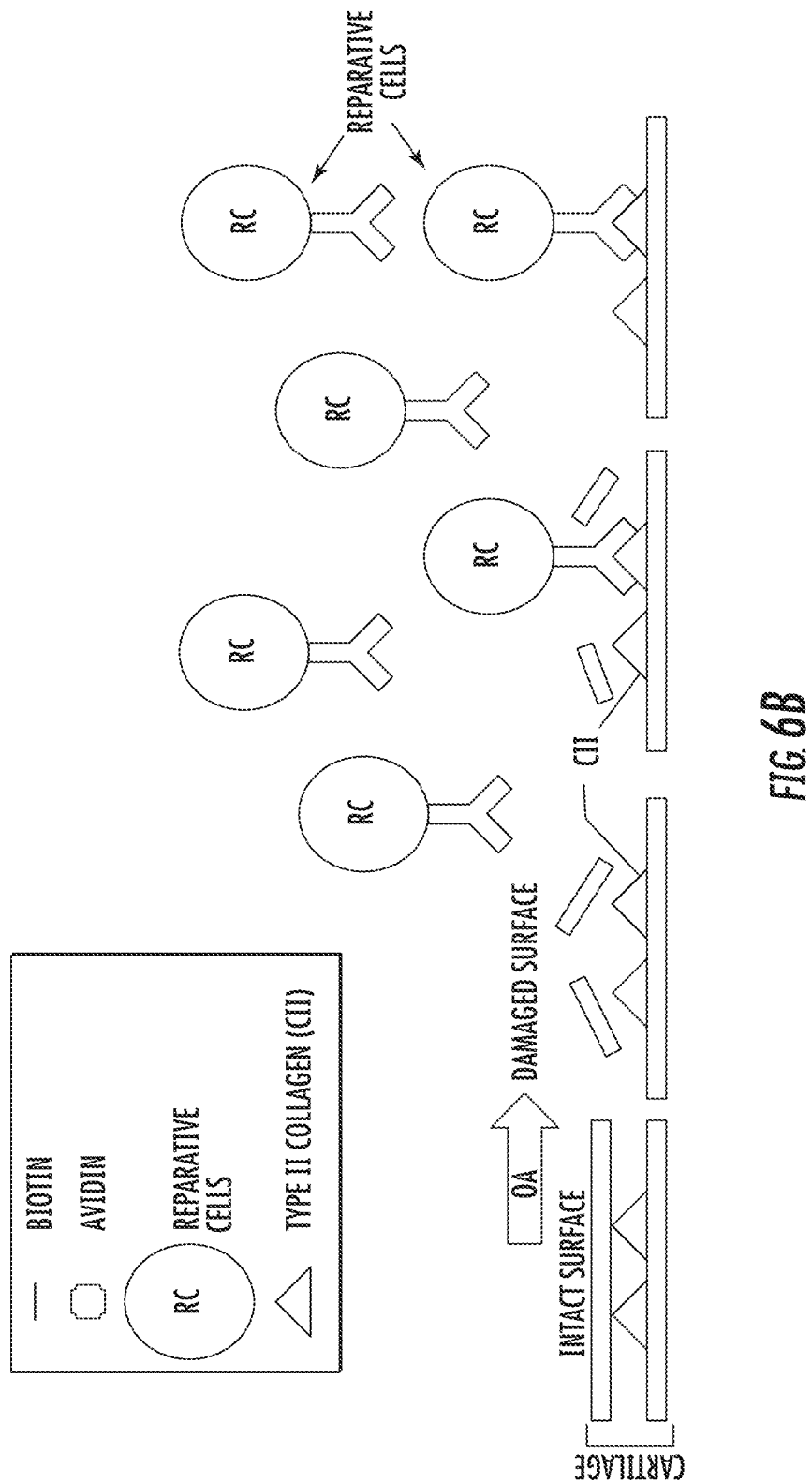
FIG. 6B is an illustration depicting the targeting of antibody-linked reparative cell (from FIG. 6A) to a site of damaged cartilage or osteoarthritis, in accordance with certain example embodiments. As illustrated, targeted recruitment and propagation to the damaged cartilage (e.g. type II collagen (CII)) or osteoarthritis lesion is achieved via the antibody attached to the reparative cell (RC), the antibody binding to exposed or newly synthesized type II collagen.

FIG. 6B is an illustration depicting the targeting of an antibody-linked reparative cell to a site of damaged cartilage or osteoarthritis, in accordance with certain example embodiments. For example, following the formation of the antibody-linked reparative cell complexes (FIG. 6A), the antibody-linked reparative cell complexes can be administered to a subject at the site of a lesion as described herein, such as by injection of the antibody-linked reparative cell complexes to a site of osteoarthritis. Administration at the site of the lesion, for example, allows the antibody-reparative cell complexes to come in to contact with the target tissue of the lesion, thereby targeting the lesion. Additionally or alternatively, the antibody-linked reparative cell complexes can be administered systemically.

Without wishing to be bound by any particular theory, it is believed that that recruitment of the antibody-linked reparative cell complexes to the site of a lesion facilitates repair of the lesion. For example, targeting of ADSCs to the site of a cartilage or osteoarthritic lesion is believed to result in repair of the lesion. The targeting of ADSCs in osteoarthritis, for example, is also believed to slow the progression of the pathological processes associated with osteoarthritis lesion development.

In certain example embodiments, the targeting antibodies described herein can be used to target nanosomes to a particular tissue, such as to a tissue lesion. For example, any of the methods described herein for targeting reparative cells, such as any of the methods illustrated in FIGS. 1-4B can be used to target nanosomes to a lesion (for illustration purposes, the nanosome can replace the reparative cell (RC) in these figures). For example, a nanosome can be biotinylated as described herein and then used in conjunction with the targeting antibody to form complexes that can be targeted to the site of a lesion (such as in FIGS. 1-4B). By using the biotin-avidin interactions described herein (and with reference to FIGS. 1-4B), for example, multiple nanosomes can be recruited to a lesion and can thereafter propagate a network of nanosomes. In certain example embodiments, an antibody can be chemically linked to the nanosome, such as in FIGS. 6A-6B, but where the reparative cell (RC) is replaced with a nano some).

The nanosome, for example, can encapsulate one or more pharmaceutical agents that can be used to treat the targeted lesion. For example, to treat mechanical stress-induced cartilage lesions, the nanosome can include therapeutically effective amounts of pharmaceutical agents that disrupt the cell signaling mechanisms involved in development of the mechanical stress-induced lesions. For example, the nanosome can include one or more pharmaceutical agents that disrupt or inhibit the NF-κB pathway. In certain example embodiments, the pharmaceutical agent is an inhibitor of IkappaB kinase-2 (IKK-2). In certain example embodiments, the pharmaceutical agent is 2-[(aminocarbonyl)amino]-5-(4-fluorophenyl)-3-thiophenecarboxamide (TPCA-1), a selective (IKK-2) inhibitor. In certain example embodiments, the pharmaceutical agent is a matrix metalloproteinase inhibitor, such as tissue inhibitor of metalloproteinases (TIMP), Batimastat, Marimastat, AG3340 (prinomastat), BAY 12-9566, MMI270, and CP-471,358. In certain example embodiments, the pharmaceutical agent is an inhibitor or scavenger of free radicals such as Tempol, catalase, and superoxide dismutase. In certain example embodiments, the nanosome can also include a carrier.

Figure 7:
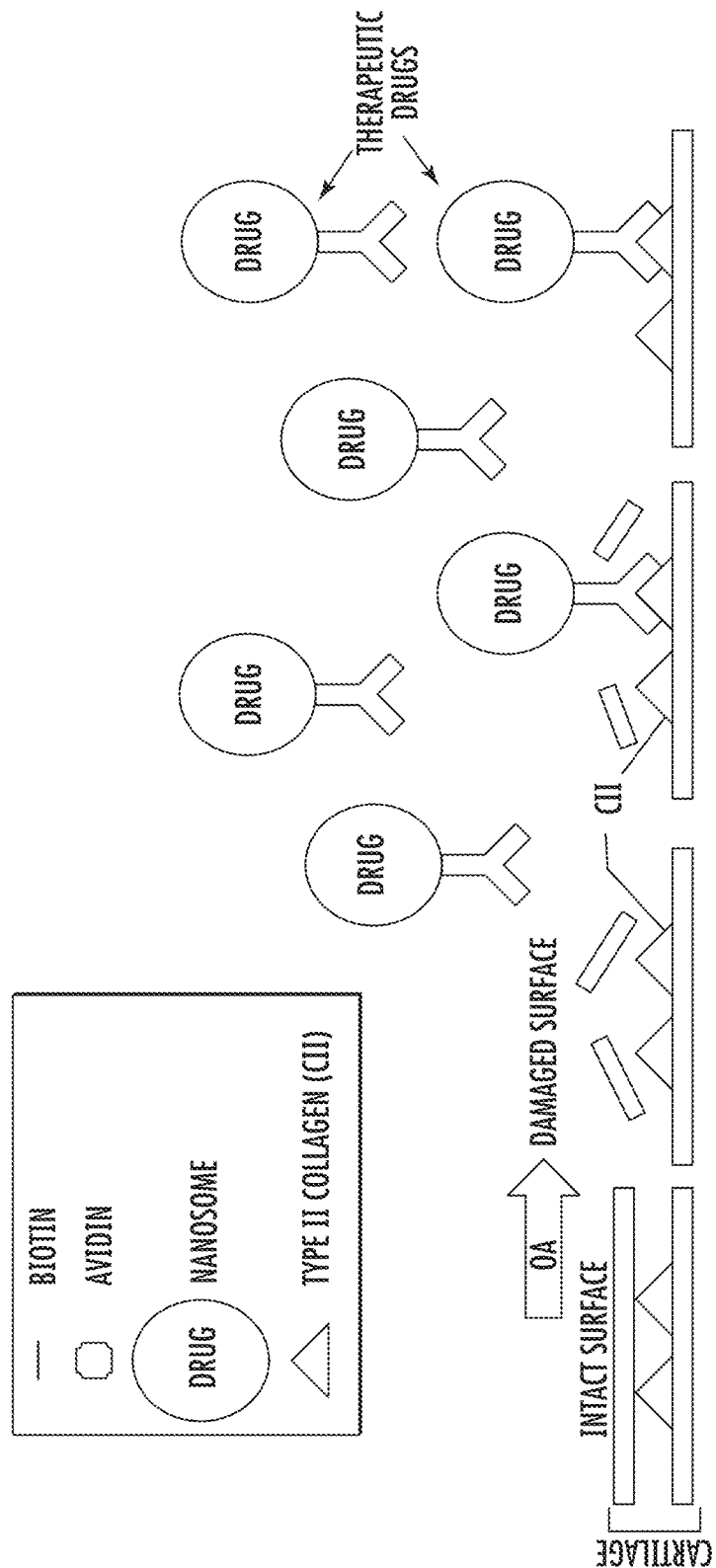
FIG. 7 is an illustration depicting the targeting of a nanosome-encapsulated drug to damaged cartilage or osteoarthritis, in accordance with certain example embodiments. As illustrated, an antibody attached to the nanosome targets the liposome to the site of damaged cartilage or osteoarthritis.

FIG. 7 is an illustration depicting the targeting of a liposome-encapsulated drug to damaged cartilage or osteoarthritis, in accordance with certain example embodiments. For example, liposomes, as well as other micellar lipid vesicles, can be included in the methods described and act as targeted, drug delivery vehicles. The methods of preparation and drug loading procedures for liposomes and the others are well-known in the art. Liposomes, for example, can contain both nonpolar and polar compounds. For example, the compounds can interact with the biocompatible and biodegradable lipid bilayer, or within the aqueous core of the liposome, respectively. As shown in FIG. 7, targeting antibodies can be chemically linked to the liposomes. Administration of the liposomes at the site of the lesion in a subject, for example, results in recruitment of the liposomes (and their contents) to the lesion (FIG. 7).

Without wishing to be bound by any particular theory, it is believed that recruitment of the liposomes to the site of a lesion and/or propagation of a liposome network at the site of the network results in delivery of the liposome's contents to the lesion. For example, as the liposomes can be recruited to a lesion, the liposome (or nanosome) lyses and releases its contents. If the liposome contains a pharmaceutical agent, for example, the pharmaceutical agent is released at the site of the lesion upon lysis of the nanosome. The pharmaceutical agent can then come in to contact with the lesion and exert its pharmacological effect. For example, if the pharmaceutical agent is TPCA-1, the TPCA1 can inhibit IKK-2 directly at the site of the lesion, without exerting any adverse systemic effects.

As those skilled in the art will appreciate, in certain example embodiments combinations of the methods and compositions described herein can be used to target cells, such as reparative cells, to the site of a lesion. Likewise, combinations of methods and compositions described herein can be used to target nanosomes to the site of a lesion. That is, any of the methods described herein in FIGS. 1-4B can be used in combination with the methods descried in FIGS. 6A-7 to deliver reparative cells and/or drug containing nanosomes to a target lesion. For example, the methods of delivering reparative cells complexes described in FIGS. 1-3 can be used in combination with the antibody-linked delivery of reparative cell complexes illustrated in FIGS. 6A-6B.

Likewise, the methods of delivering reparative cells complexes described in FIGS. 4A-5D can be used in combination with the antibody-linked delivery of reparative cell complexes or drug containing liposomes as illustrated in FIGS. 6A-6B. Further, either of these combinations can also be used in combination with the delivery of liposomes described in FIG. 7. In such embodiments, multiple reparative cells can be targeted to the site of a lesion, along with pharmaceutical agents that can be delivered (via the liposomes) at the site of the lesion. In certain example embodiments, the effect of combining the one or more methods can be greater than any of the methods when used individually. For example, lesion damage may be improved by about 10-70% for a combined treatment verses an individual treatment, such as about 10%, 15%, 20%, 25%, 30%, 35%, 40%, 45%, 50%, 55%, 60%, 65%, 70%, 75%, or more improved.

As those skilled in the art will appreciate based on this disclosure, any antibody or combination of antibodies that includes affinity for an epitope present at a lesion and/or an epitope present on a reparative cell, for example, can be used in accordance with the method described herein. In certain example embodiments, the targeting antibody described herein comprises a heavy chain amino acid sequence having the sequence set forth as SEQ ID NO. 1 or an antigen binding fragment thereof. In certain example embodiments, the amino acid sequence of the heavy chain may be 85, 86, 87, 88, 89, 90, 91, 92, 93, 94, 95, 96, 97, 98, or 99% identical to the amino acid sequence set forth as SEQ ID NO. 1.

In certain example embodiments, the targeting antibody described herein further comprises a light chain having the amino acid set forth as SEQ ID NO. 2 (or an antigen fragment thereof). In certain example embodiments, the amino acid sequence of the light chain may be 85, 86, 87, 88, 89, 90, 91, 92, 93, 94, 95, 96, 97, 98, or 99% identical to the amino acid sequence set forth as SEQ ID NO. 2.

In certain example embodiments, the targeting antibody described herein comprises a heavy chain encoded by the nucleotide sequence set forth as SEQ ID NO. 3. In certain example embodiments, the targeting antibody described herein comprises a heavy chain encoded by a nucleotide sequence having 85, 86, 87, 88, 89, 90, 91, 92, 93, 94, 95, 96, 97, 98, or 99% sequence identity to the nucleotide sequence set forth as SEQ ID NO. 3.

In certain example embodiments, the light chain of the targeting antibody described herein is encoded by the nucleotide sequence set forth as SEQ ID NO. 5. In certain example embodiments, the light chain of the targeting antibody described herein is encoded by a nucleotide sequence that is 85, 86, 87, 88, 89, 90, 91, 92, 93, 94, 95, 96, 97, 98, or 99% identical to the nucleotide sequence set forth as SEQ ID NO. 4.

In certain example embodiments targeting antibodies, or antigen-binding fragments thereof, comprise an VH and an VL amino acid sequence pair (VH/VL) comprising any of the VH amino acid sequences listed in Table 1 paired with any of the VL amino acid sequences listed in Table 1. According to certain example embodiments, targeting antibodies, or antigen-binding fragments thereof, comprises an VH/VL amino acid sequence pair contained within the antibody listed in Table 1. In certain embodiments, the VH/VL amino acid sequence pair is SEQ ID NO:6/14.

In certain example embodiments targeting antibodies, or antigen-binding fragments thereof, comprise a heavy chain CDR1 (HCDR1) comprising an amino acid sequence set forth as SEQ ID NO:8 or a substantially similar sequence thereof having at least 90%, at least 95%, at least 98% or at least 99% sequence identity.

In certain example embodiments targeting antibodies, or antigen-binding fragments thereof, comprise, or antigen-binding fragments thereof, comprise a heavy chain CDR2 (HCDR2) comprising an amino acid sequence set forth as SEQ ID NO:10, or a substantially similar sequence thereof having at least 90%, at least 95%, at least 98% or at least 99% sequence identity.

In certain example embodiments targeting antibodies, or antigen-binding fragments thereof, comprise a heavy chain CDR3 (HCDR3) comprising an amino acid sequence set forth as SEQ ID NO:12, or a substantially similar sequence thereof having at least 90%, at least 95%, at least 98% or at least 99% sequence identity.

In certain example embodiments targeting antibodies, or antigen-binding fragments thereof, comprise a light chain CDR1 (LCDR1) comprising an amino acid sequence set forth as SEQ ID NO:16, or a substantially similar sequence thereof having at least 90%, at least 95%, at least 98% or at least 99% sequence identity.

In certain example embodiments targeting antibodies, or antigen-binding fragments thereof, comprise a light chain CDR2 (LCDR2) comprising an amino acid sequence set forth as SEQ ID NO:18, or a substantially similar sequence thereof having at least 90%, at least 95%, at least 98% or at least 99% sequence identity.

In certain example embodiments targeting antibodies, or antigen-binding fragments thereof, comprise a light chain CDR3 (LCDR3) comprising an amino acid sequence set forth as SEQ ID NO:20, or a substantially similar sequence thereof having at least 90%, at least 95%, at least 98% or at least 99% sequence identity.

In certain example embodiments targeting antibodies, or antigen-binding fragments thereof, comprise an HCDR3 and an LCDR3 amino acid sequence pair (HCDR3/LCDR3) comprising the HCDR3 amino acid sequence listed in Table 1 paired with the LCDR3 amino acid sequence listed in Table 1. According to certain example embodiments, the targeting antibodies, or antigen-binding fragments thereof, the HCDR3/LCDR3 amino acid sequence pair is SEQ ID NOs: 12/20.

In certain example embodiments targeting antibodies, or antigen-binding fragments thereof, comprise a set of six CDRs (i.e., HCDR1-HCDR2-HCDR3-LCDR1-LCDR2-LCDR3) contained within any of the exemplary E4 antibody listed in Table 1. In certain embodiments, the HCDR1-HCDR2-HCDR3-LCDR1-LCDR2-LCDR3 amino acid sequences set is SEQ ID NOs: 8-10-12-16-18-20.

In certain example embodiments targeting antibodies, or antigen-binding fragments thereof, comprise a set of six CDRs (i.e., HCDR1-HCDR2-HCDR3-LCDR1-LCDR2-LCDR3) contained within the VH/VL amino acid sequence pair as defined the exemplary E4 antibody listed in Table 1. For example, certain example embodiments targeting antibodies, or antigen-binding fragments thereof, comprise the HCDR1-HCDR2-HCDR3-LCDR1-LCDR2-LCDR3 amino acid sequences set contained within a VH/VL amino acid sequence of SEQ ID NOs: 6/14 Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

In certain example embodiments, nucleic acid molecules can be used to encode targeting antibodies or portions thereof. For example, in certain example embodiments nucleic acid molecules encode any of the VH amino acid sequences listed in Table 1; in certain embodiments the nucleic acid molecule comprises a polynucleotide sequence set forth as SEQ ID NO:5, or a substantially similar sequence thereof having at least 90%, at least 95%, at least 98% or at least 99% sequence identity thereto.

In certain example embodiments, a nucleic acid molecule encodes the VL amino acid sequences listed in Table 1; in certain embodiments the nucleic acid molecule comprises a polynucleotide sequence set forth as SEQ ID NO:13, or a substantially similar sequence thereof having at least 90%, at least 95%, at least 98% or at least 99% sequence identity thereto.

In certain example embodiments, a nucleic acid molecule encodes the HCDR1 amino acid sequences listed in Table 1; in certain embodiments the nucleic acid molecule comprises the nucleic acid molecule comprises a polynucleotide sequence set forth as SEQ ID NO:7, or a substantially similar sequence thereof having at least 90%, at least 95%, at least 98% or at least 99% sequence identity thereto.

In certain example embodiments, a nucleic acid molecule encodes the HCDR2 amino acid sequences listed in Table 1; in certain embodiments the nucleic acid molecule comprises a polynucleotide sequence set forth as SEQ ID NO:9, or a substantially similar sequence thereof having at least 90%, at least 95%, at least 98% or at least 99% sequence identity thereto.

In certain example embodiments, a nucleic acid molecule encodes the HCDR3 amino acid sequences listed in Table 1 in certain embodiments the nucleic acid molecule comprises a polynucleotide sequence set forth as SEQ ID NO:11, or a substantially similar sequence thereof having at least 90%, at least 95%, at least 98% or at least 99% sequence identity thereto.

In certain example embodiments, a nucleic acid molecule encodes the LCDR1 amino acid sequences listed in Table 1; in certain embodiments the nucleic acid molecule comprises a polynucleotide sequence set forth as SEQ ID NO:15, or a substantially similar sequence thereof having at least 90%, at least 95%, at least 98% or at least 99% sequence identity thereto.

In certain example embodiments, a nucleic acid molecule encodes the LCDR2 amino acid sequences listed in Table 1; in certain embodiments the nucleic acid molecule comprises a polynucleotide sequence set forth as SEQ ID NO:17, or a substantially similar sequence thereof having at least 90%, at least 95%, at least 98% or at least 99% sequence identity thereto.

In certain example embodiments, a nucleic acid molecule encodes the LCDR3 amino acid sequences listed in Table 1; in certain embodiments the nucleic acid molecule comprises a polynucleotide sequence set forth as SEQ ID NO:19, or a substantially similar sequence thereof having at least 90%, at least 95%, at least 98% or at least 99% sequence identity thereto.

In certain example embodiments, a nucleic acid molecule encodes a VH, wherein the VH comprises a set of three CDRs (i.e., HCDR1-HCDR2-HCDR3), wherein the HCDR1-HCDR2-HCDR3 amino acid sequence set is set forth as SEQ ID NOs: 8-10-12.

In certain example embodiments, a nucleic acid molecule encodes a VL, wherein the VL comprises a set of three CDRs (i.e., LCDR1-LCDR2-LCDR3), wherein the LCDR1-LCDR2-LCDR3 amino acid sequence set is set forth as SEQ ID NOs:16-18-20.

In certain example embodiments, a nucleic acid molecule encodes both an VH and an VL, wherein the VH comprises an amino acid sequence set forth as SEQ ID NO:6, and wherein the VL comprises an amino acid sequence of any of the VL amino acid sequence set forth as SEQ ID NO:14. In certain embodiments, the nucleic acid molecule comprises a polynucleotide sequence set forth as SEQ ID NO:5, or a substantially similar sequence thereof having at least 90%, at least 95%, at least 98% or at least 99% sequence identity thereto, and a polynucleotide sequence set forth as SEQ ID NO:13, or a substantially similar sequence thereof having at least 90%, at least 95%, at least 98% or at least 99% sequence identity thereto. In certain embodiments according to this aspect of the invention, the nucleic acid molecule encodes an VH and VL, wherein the VH and VL can be both derived from the same E4 antibody listed in Table 1.

In certain example embodiments, recombinant expression vectors are capable of expressing a polypeptide comprising a heavy or light chain variable region of an E4 antibody. For example, in certain example embodiments, recombinant expression vectors comprise any of the nucleic acid molecules mentioned above, i.e., nucleic acid molecules encoding any of the VH, VL, and/or CDR sequences as set forth in Table 1. Also, in certain example embodiments are host cells into which such vectors have been introduced, as well as methods of producing the antibodies or portions thereof by culturing the host cells under conditions permitting production of the antibodies or antibody fragments, and recovering the antibodies and antibody fragments so produced.

In certain example embodiments, a targeting antibody or fragment thereof is placed in a pharmaceutical composition comprising the targeting antibody or fragment thereof and a pharmaceutically acceptable carrier. In a related aspect, the invention features a composition which is a combination of an E4 antibody and a second therapeutic agent. In certain example embodiments, a targeting antibody or fragment thereof, is used in the manufacture of a medicament for the treatment of a disease or disorder (e.g., a cartilage lesion). In an example embodiment, a compound comprising a targeting antibody or antigen-binding fragment, as disclosed herein, for can be used in a medical application, such as a method of treatment.

The invention furthermore provides an antibody or antigen-binding fragment, wherein the antibody or antigen-binding fragment thereof binds to the same epitope on human E4 as a reference antibody comprising an VH/VL amino acid sequence pair as set forth in Table 1. In another aspect, the antibody or antigen-binding fragment binds to the same epitope on human E4 as a reference antibody comprising an VH/VL amino acid sequence pair selected from the group consisting of SEQ ID NOs: 6/18.

EXAMPLES

The following examples further illustrate the invention but should not be construed as in any way limiting its scope.

In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1—Evaluation of Cartilage Explants In Vitro

In this study, we propose that a two-step coating method can be used as a paradigm for the delivery and recruitment of reparative cells to a specific tissue site by recognition of target molecules (exposed type II collagen: CII) in the cartilage extracellular matrix (e.g., FIG. 1). First, biotinylated-MabCII is injected into the joint space and allowed to bind to the exposed type II collagen in the damaged or degenerated cartilage. Next, biotinylated reparative cells, pre-treated with avidin to occupy some of the biotinylated sites, are injected. By using fluorescently labeled cells, we can monitor the explants to detect specific localization and dependency of this process on targeting MabCII antibody. By using devitalized cartilage, we can monitor the differentiation status of the cells binding to the explants.

Materials and Methods

Preparation of Monoclonal Antibodies to Type II Cartilage

B6-DR4+/− (DRB1*0401) transgenic mice were raised in the animal facility at the Veterans Administration Medical Center (Memphis, Tenn.) in a specific pathogen-free environment. The production of the chimeric genes and the B10.M-DR4 transgenic mouse has been previously described [11]. Native bovine type II collagen (bCII) was solubilized from articular cartilage by limited proteolysis with pepsin and purified by repeated differential salt precipitation as previously described [12]. Six- to eight-week-old mice were immunized with bCII for the induction of arthritis [13]. The CII was dissolved in cold 10 mM acetic acid by stirring overnight at 4° C. and was emulsified at a 1:1 (v/v) ratio with CFA (Life Technologies, Gaithersburg, Md.), as previously described (14). Mice were immunized s.c. at the base of the tail with 100 m of CII emulsified with complete Freund's adjuvant and boosted three weeks later with CII emulsified in incomplete Freund's adjuvant and spleens were obtained for hybridoma preparation at nine weeks following primary immunization. Mice were bled at 5 weeks after the first immunization and antibody titers were determined in a bCII ELISA. Hybridomas were generated as described [15] by fusing spleen cells from mice showing high specific titers to bCII with the myeloma cell line AG8 using PEG/DMSO solution Hybri-Max 50% (Sigma-Aldrich). Hybridoma clones were tested for specificity to bCII and cloned twice by limiting dilution. Antibodies were also tested for cross-reactivity by ELISA against type II collagen from mouse, pig and human species and recognized all of these collagens equally well compared to bovine type II collagen. Purified MabCII from culture supernatants of the E4-D4 (E4) clone was obtained by chromatography on Protein G Sepharose Fast Flow (Sigma Aldrich).

Antibody Sequencing (E4 Antibody)

Antibody sequencing was performed by Creative Biolabs (CBL) of the E4 clone, described herein. Three tubes of total RNA were provided to CBL of the AG8 hybridoma cells, and antibody genes were cloned therefrom. The intact heavy chain (HC) gene was cloned By RT-PCR using the degenerate primers designed by CBL. The genes were cloned into T vector for DNA sequencing locally. The intact HC gene is shown below. Similarly, the intact KC gene was cloned by RT-PCR using the degenerate primers designed by CBL. The genes were cloned into T Vector for DNA sequencing locally. According to the sequences, the mAb has mouse IgG2a heavy chain and kappa Light chain.

The full-length amino acid (AA) sequence of the E4 heavy chain (including VH and CH) is set forth as SEQ ID NO:1, which can be encoded by a nucleic acid (NA) sequence set forth as SEQ ID NO:3. The full-length amino acid (AA) sequence the E4 light chain (including VL and CL) is set forth as SEQ ID NO:2, which can be encoded by a nucleic acid sequence set forth as SEQ ID NO:4.

Table 1 sets forth sequence identifiers of a nucleic acid (NA) sequence encoding, and in parentheses an amino acid (AA) sequence of, a heavy or light chain variable region (VH or VL, respectively), or a heavy or light chain CDR (HCDR and LCDR, respectively) of the E4 monoclonal antibody.

| SEQ ID NOs: | | | | | | | |
|---|---|---|---|---|---|---|---|
| HCVR NA (AA) | HCDR1 NA (AA) | HCDR2 NA (AA) | HCDR3 NA (AA) | LCVR NA (AA) | LCDR1 NA (AA) | LCDR2 NA (AA) | LCDR3 NA (AA) |
| 5 (6) | 7 (8) | 9 (10) | 11 (12) | 13 (14) | 15 (16) | 17 (18) | 19 (20) |

Biotinylation of Monoclonal Antibodies to Type II Cartilage (E4 Clone)

Type II collagen monoclonal antibody (MabCII) at a concentration of 1 mg/mL was buffer exchanged with phosphate buffered saline (PBS). The linking reagent NHS-PEG4-Biotin (Thermo Scientific) was then brought up in distilled water to a recommended 20-fold molar excess of Biotin per mg/mL of MabCII. The biotinylated MabCII sample was then added to a Zeba spin desalting column (Thermo Scientific) column and centrifuged at 1000×g for 2 minutes in order to remove excess biotin reagent. The collected flow-through solution was the purified sample. As a control, irrelevant monoclonal mouse IgG antibody of the same subclass (Isotype Control from R&D Systems, Inc.) was similarly prepared.

Cell Labeling with PEG-Biotin

A stock solution of DSPE-PEG(2000) Biotin (1,2-distearoyl-sn-glycero-3-phosphoethanolamine-N-[biotinyl (polyethylene glycol)-2000] ammonium salt) (PE-PEG-Biotin; Avanti Polar Lipids, Inc) (10 mg/ml) was dried under nitrogen and then vacuumed dried for 15 minutes. The dried PE-PEG-Biotin was then brought up in 10 microliters of dimethylformamide and then 250 mM Sucrose and 1 mM HEPES, pH 7.2 was added to give a stock PE-PEG-Biotin solution of 1 mM. The solution was incubated for 5 minutes at 37° C., then sonicated for 5 minutes in a bath sonicator, and finally, was heated for 5 minutes in a water bath at 50° C.

The reparative cells (isolated chondrocytes or chondrogenically differentiated ADSCs) previously labeled with a fluorescent dye (Vivotrack 680: PerkinElmer, MA), were re-suspended at $1 \times 10^6$ cells/ml in fresh serum-free medium with 250 mM sucrose, 1 mM HEPES, and 1 mM CaCl2. The PE-PEG-Biotin stock solution (1 mM) was then added to the various tubes at 25 µM final concentration and incubated for 60 minutes to allow PE-PEG-Biotin integration into the cell membranes. Neutravidin was dissolved in PBS and added to the PE-PEG-Biotin labeled cells at a final concentration of 1204 of Neutravidin. The tubes were then allowed to incubate on a rocker platform for 30 minutes at 37° C. for binding. After incubation, the cells were centrifuged, supernatants were discarded, and serum-free medium was added and the cells vortexed ready to incubate with the cartilage explants.

Preparation of Cartilage Tissue Explants

Cartilage explants were harvested from the articular cartilage of femoral condyles of domestic pigs ranging from 25 to 30 kilograms and were punched from cartilage explants taken from the surface of articular cartilage with a 6 mm dermal punch to provide equivalent surface areas. The cartilage explants were divided into two groups for incubation with biotinylated Mab; one group that would be mechanically damaged and one group with no damage (normal). In order to simulate damaged cartilage in the exposed type II collagen group, a surgical scalpel was used in order to create a rough, shallow scratch down the center of each of the cartilage explants used in this group. The group with no inflicted damage was left intact with normal cartilage surfaces. Some of the cartilage explants were enzymatically digested for individual cell isolation as previously described [7]. The ADSCs were obtained from pig adipose tissue and cultured under chondrogenic conditions as previously described [9].

The cartilage explants were incubated with biotinylated antibodies (MabCII or isotype control antibodies; MabCont) for 1 hour at 37° C. After washing the unbound antibodies, the explants were re-punched with a 4 mm dermal punch to remove the mechanically damaged sides and incubated with fluorescent (Vivotrack 680) avidin/biotinylated reparative cells for 1 hour at 37° C. After incubation, the cartilage explants were washed with PBS and scanned using a Lumina II (Caliper Life Science, Hopkinton, Mass.) in vitro imaging system (IVIS) to visualize the localization of reparative cells.

For evaluation of gene expression of the reparative cells attaching to cartilage explants with the two step MabCII, biotin-avidin system described above, cartilage explants were devitalized by freeze thawing and washed three times before incubation with biotinylated MabCII and avidin/biotinylated chondrocytes or avidin/biotinylated chondrogenically differentiated ADSC cells as described above. After washing to remove unbound cells, the cells bound to the explants were incubated for one week in complete F12K culture medium with 10% FCS. The explants were then washed and the RNA extracted with Trizol for quantitative polymerase chain reaction (PCR) for the cartilage specific-type II collagen expression. Quantitative gene expression was analyzed by PCR using primers specific for type II collagen (Col-II) and the housekeeping gene glyceraldehyde-3-phosphate dehydrogenase (GAPDH). Gene expression was calculated as $2^{-\Delta\Delta CT}$ after normalization to GAPDH expression. For some experiments gene expression from avidin/biotinylated cells that were incubated in standard tissue culture wells or incubated with cartilage with no antibody for the same period of time were set as 1+/− standard error of the mean (SEM) and compared to same type of cells binding to the cartilage explants.

Results

Binding to Localized Cartilage Lesions

Figure 8:
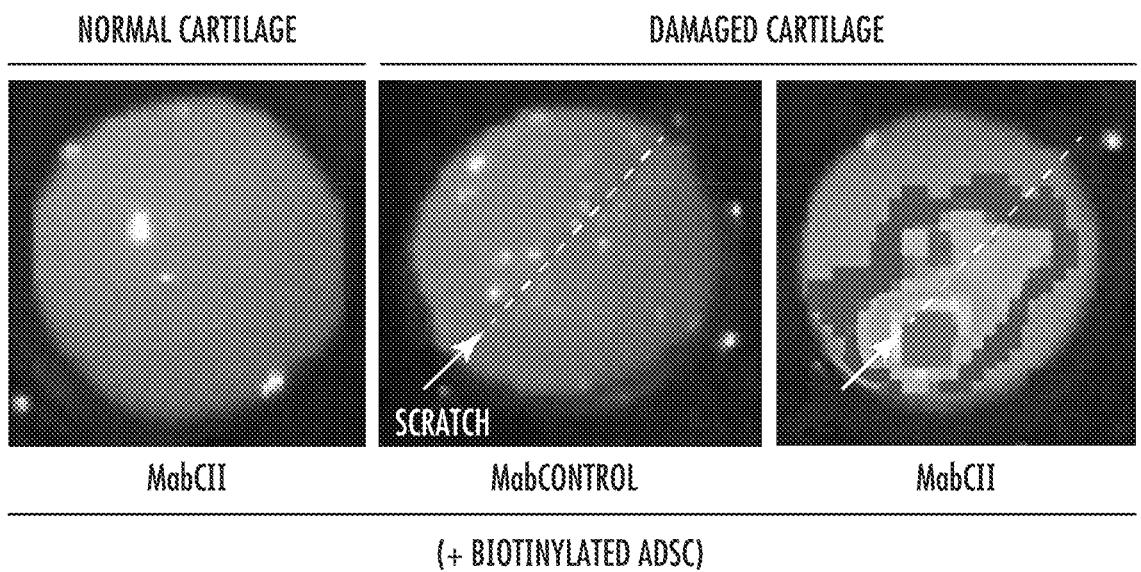
FIG. 8 is a series of IVIS® scanned images of cartilage explanted and treated with fluorescent avidin/biotinylated adipocyte derived stem cells (ADSCs). Articular cartilage explants were physically scratched (B and C) to mimic a damaged cartilage tissue, or (A) without scratching for intact tissue, then incubated for 1 hr with biotinylated antibodies (A and C: MabCII ((E4) clone), B: MabControl) and then were washed with PBS. After a secondary punch with a 4 mm biopsy punch to remove the sides that were mechanically damaged from the initial harvesting, the cartilage tissues were incubated with fluorescent avidin/biotinylated ADSCs, washed and then scanned by optical imaging. As shown, only MabCII targets ADSC to damaged cartilage explants.

As shown in FIG. 8, fluorescent avidin/biotinylated ADSC cells binding to normal articular cartilage were not detectable even after incubation of the normal cartilage with MabCII (left panel). Similarly, the use of MabControl did not result in any cell binding to the damaged cartilage (FIG. 8. Center panel). A significant amount of reparative cells binding is only seen in the scratch location of the damaged cartilage incubated with MabCII (FIG. 8, right panel). This binding shows that this method is specific for binding of cells to damaged cartilage. Experiments conducted with isolated articular chondrocytes showed the same specificity of binding (data not shown) offering a selection of reparative cells using this method for cartilage repair. Only the articular cartilage scratched and treated with MabCII binds with the ADSCs.

Figure 9A:
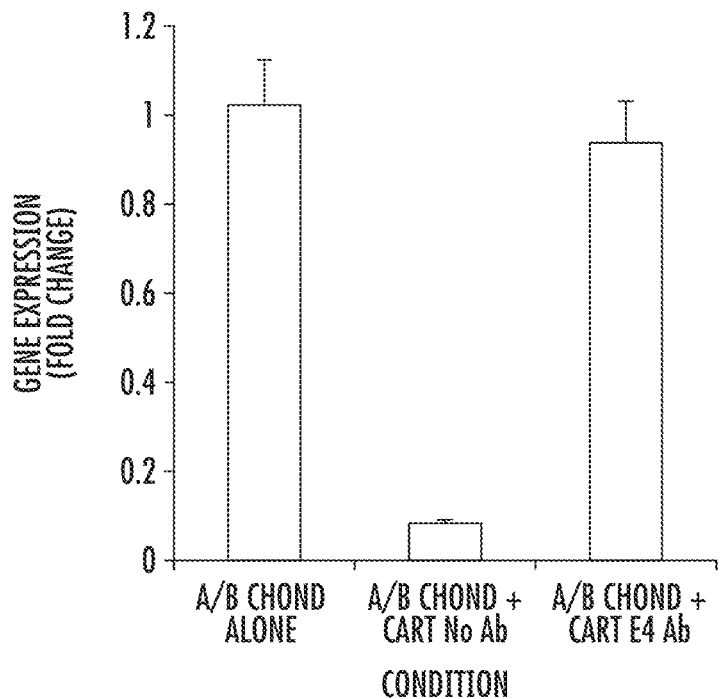
FIGS. 9A-9B are graphs showing gene expression of cartilage explants that were treated with avidin/biotinylated chondrocytes (FIG. 9A) or avidin/biotinylated ADSCs (FIG. 9B). Devitalized articular cartilage explants were scratched to mimic a damaged cartilage tissue, then incubated for 1 hr with or without biotinylated MabCII and then were washed with PBS. The cartilage tissues were then incubated for one week with avidin/biotinylated chondrocytes or ADSC cells, washed and then RNA was extracted for PCR measurements of type II collagen. Results are shown as relative change in gene expression after normalization to the housekeeping gene Glyceraldehyde-3-phosphate dehydrogenase (GAPDH) and compared to control cultures set as "one." As shown, chondrocytes (FIG. 9A) or ADSC (FIG. 9B) targeted with MabCII to damaged cartilage explants continue to express type II collagen (Col2a1). Very little type II collagen expression is seen in explants treated with non-targeted cells.
Figure 9B:
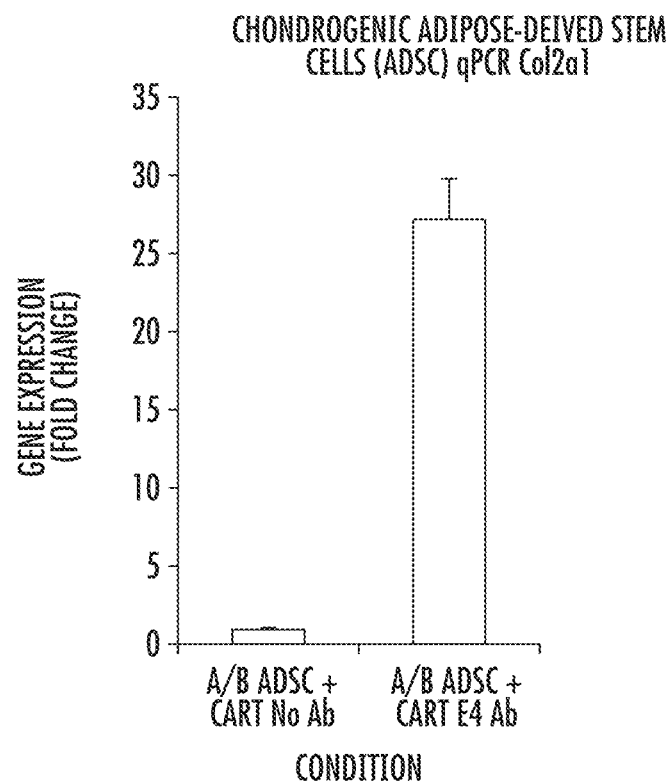

Evaluation of Chondrocyte and ADSC Gene Expression after Cartilage Explant Binding Gene expression of type II collagen of the chondrocytes or ADSCs binding to devitalized cartilage explants was analyzed at the end of the one-week incubation (FIG. 9). As shown in FIG. 9, very little expression of type II collagen was seen in samples taken from explants that were incubated with cells in the absence of antibody corresponding to the small number of cells that bind under these conditions. Devitalized cartilage alone did not show any evidence of type II collagen expression (data not shown). For explants incubated with articular chondrocytes, the expression of CII was equivalent to these cells maintained without cartilage in standard tissue culture during this time.

DISCUSSION

We have used MabCII to target theranostic near-infrared fluorescent nanosized-liposomes (nanosomes) for diagnosis and treatment of early OA. These immunoliposomes bind to damaged but not normal cartilage. Using these reagents, we can quantitate exposure of type II collagen during cartilage degradation in individual joints in vivo in a spontaneous model of OA in guinea pigs as well as in a mouse PTOA model of knee overload [7, 8]. We now show that these antibodies can also be used as an initiation point for recruitment of reparative cells to an early OA lesion. By employing an avidin-biotinylation complex on the surface of reparative cells injected into the synovial cavity, the cells are induced to bind to the early OA lesion where the biotinylated antibodies are localized. Display of the avidin/biotin complex on the cells localizing to the bound antibody, in turn recruits other avidin/biotinylated reparative cells thereby propagating accumulation to the area of the OA lesion. The bound cells maintained differentiation of type II collagen expression and their binding was dependent upon the presence of MabCII. Our data supports that this methodology permits specific targeting of reparative cells and re-surfacing of the damaged cartilage surface.

Example 2—Evaluation of Type II Collagen Antibody-Targeted Nanosomes (E4 Clone)

We hypothesized that inhibition of IKK-2 would be beneficial to prevent stimulation of MMP-13 and other MMPs and the progression of arthritis. The selective inhibitor of human IKK-2, 2-[(aminocarbonyl) amino]-5-(4-fluorophenyl)-3-thiophenecarboxamide (TPCA-1), has shown to reduce proinflammatory mediators such as TNF-α in collagen-induced arthritis in mice, an inflammatory autoimmune model [20]. We hypothesized that inhibition of IKK-2 could decrease stimulation of MMP activity in a model of post-traumatic osteoarthritis (PTOA) in the mouse knee. We have focused our efforts on finding a targeted delivery system for administration of an effective NF-κB inhibitor to both confirm the role of NF-κB in PTOA and to inhibit OA progression in its early stages of OA.

Hence, the purpose of this study was to develop type II collagen antibody-targeted nanosomes, encapsulating TPCA-1 an NF-κB inhibitor, which would specifically localize to defects in articular cartilage where type II collagen is exposed after mechanical loading. The burst lysis of the bound nanosomes at the site of early damage then locally delivers a drug, the delivery of which is believed to slow the progression of cartilage breakdown and delay or prevent the development of PTOA.

Materials and Methods
Preparation of Targeted Nanosomes

Targeted nanosomes were generated from lipids and conjugated to purified E4-D4 (E4) monoclonal antibody to type II collagen that was developed from a hybridoma isolated from mice immunized with type II collagen. Briefly, the lipid film which contained dioleoyl-sn-glycero-3-phosphocholine (DOPC), cholesterol, 1,2-distearoyl-sn-glycero-3-phosphoethanolamine-N-[maleimide (polyethylene glycol) 2000] (DSPE-PEG-maleimide) and TPCA-1 was rehydrated with phosphate buffered saline (PBS) and sonicated. The rehydrated lipids were repeatedly extruded through a 200 nm porous membrane to generate 200 nm 1-3 walled nanosomes. The E4 MabCII was thiolated using Traut's reagent, then mixed with the nanosomes for conjugation. After conjugation, the reaction mixture was chromatographed on a Sepharose CL-4B column to separate the free antibodies from those conjugated to the liposomes. The E4 MabCII was also conjugated to the near infrared dye XenoLight CF 680 (PerkinElmer) used for the final quantitative imaging of arthritic damage.

Treatments

The C57BL/6 mice aged 9 weeks (n=18) were divided into three different treatment groups receiving empty nanosomes (Control), TPCA-1 solution (100 uM) and TPCA-1-loaded nanosomes (containing 100 μM of TPCA-1). Each mouse received an intravenous injection of 100 μL, of solution retro-orbitally 24 hours prior to the first mechanical loading and two additional injections at 96 hr and 192 hr following the first loading interval. A group of mice that did not receive any treatment served as a normal non-loaded control. The mechanically-loaded groups received a total of six mechanical loading episodes.

Mechanical Loading to Induce OA

A loading episode of 40 cycles of 9 N compressive loading was given three times a week over a period of two weeks using conditions adapted from Poulet et al. [21]. Mice of equivalent weight (<10% variance) were anesthetized with 2% isofluorane. The left leg of each mouse was positioned within a Bose ElectroForce 3200 electromagnetic testing system: the proximal tibia rested in the upper cup with the dorsiflexed ankle inserted into the bottom cup. The load was administered with a static offset load of 2 N used to maintain contact between the specimen and the load cell. All animal protocols were approved by the VA IACUC.

Fluorescence Scanning and Analysis

At the completion of the two-week loading period, mice were injected retro-orbitally with 100 μL composite mixture of 50 μL of 1 mg/ml E4 monoclonal antibody to type II collagen MabCII680 labeled with Xenolight CF 680 fluorescent dye and 50 μL of MMPSense-750 (Perkin-Elmer, Waltham, Mass.), a substrate that fluoresces when cleaved by MMPs. After 24 hours, the mice were anesthetized and the knee joints were optically scanned for each type of fluorescence using a Lumina XR Imaging System (Perkin Elmer, Waltham, Mass.).

Results

Figure 10A:
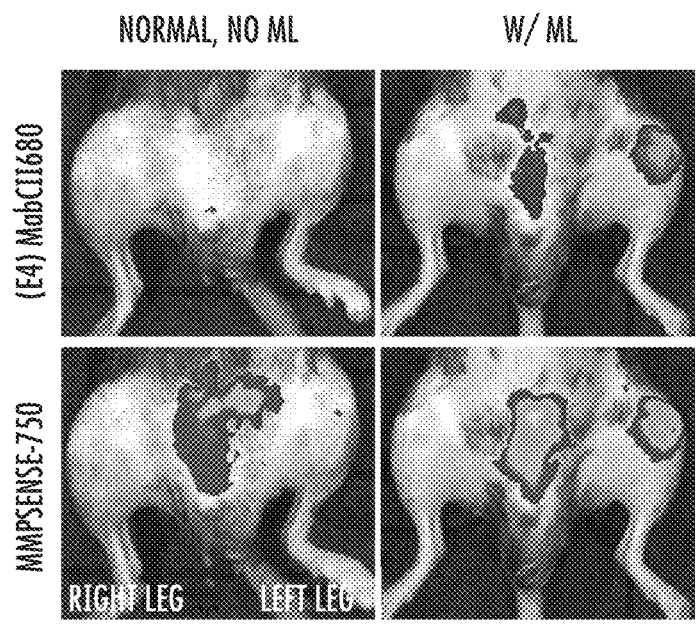
FIGS. 10A-10B are series of optically scanned images of mice where the left knee was mechanically loaded to create cartilage damage and experimentally treated by intravenous injection with E4 MabCII-targeted nanosomes loaded with the drug 2-[(aminocarbonyl)amino]-5-(4-fluorophenyl)-3thiophenecarboxamide (TPCA-1), soluble TPCA-1 or targeted empty nanosomes (Control) and compared to normal mice.
Figure 10B:
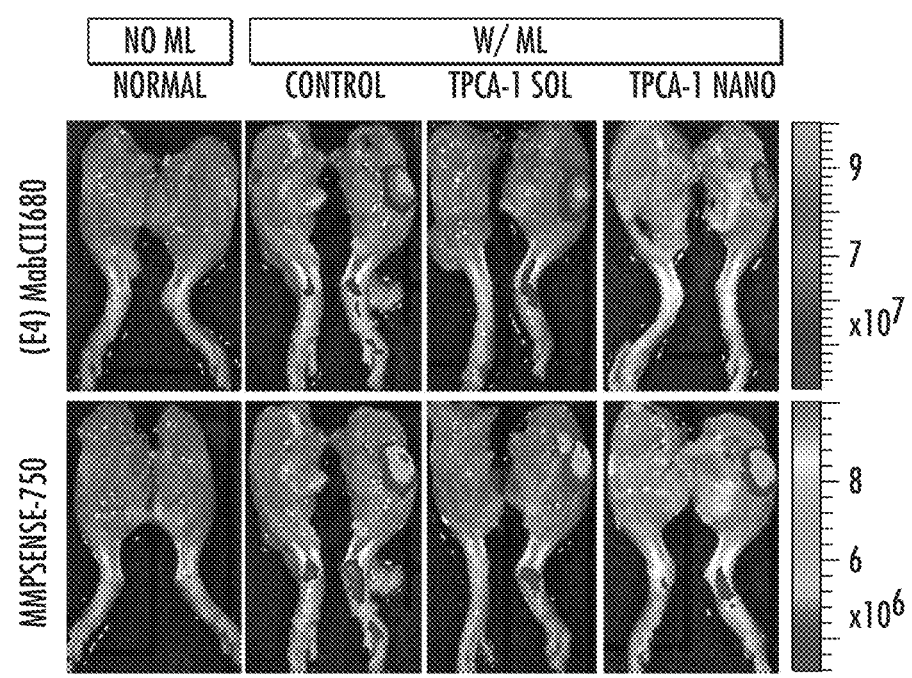

Optical scanning was used to visualize the systemic distribution of the MabCII680 in the mechanically loaded mouse knee (FIG. 10A and FIG. 10B). As shown in FIG. 10A and FIG. 10B, E4 MabCII labeled with the Xenolight 680 dye was not detectable in the knees of normal mice. Measurable 680 or MMPSense750 fluorescence was only seen in compressively loaded knees of mice injected with fluorescent MabCII while little fluorescence was detected in the contralateral knee of the same mouse (FIG. 10A and FIG. 10B). This binding thus shows specificity for the damaged cartilage in the loaded left knee (LK) as we have reported previously [22].

Figure 11A:
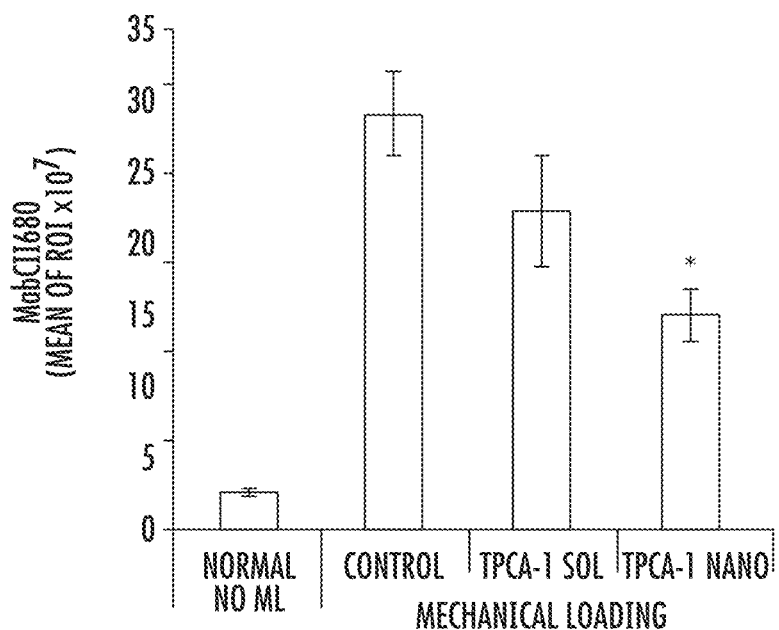
FIGS. 11A-11B are a series of graphs showing the quantitation of fluorescence from the region of interest (ROI) in the left knees of mechanically loaded (ML) or normal mice shown in FIGS. 10A and 10B, respectively, that were intravenously injected with MabCII680 fluorescent antibody (FIG. 11A) and MMPSense-750 fluorescent substrate (FIG. 11B) for MMP activity. The amount of fluorescence shown for MabCII680 (FIG. 11A) represents the amount of type II collagen that is exposed and available for antibody binding while the amount of fluorescence shown by MMPSense (FIG. 11B) represents the enzymatic activity of MMPs. This result indicates that the group treated with targeted nanosomes had significantly less cartilage damage or MMP activity than other groups. The mean+/−SEM of the ROI was calculated for each group plotted. Student's t tests were performed to determine statistical significance. A P-value of less than 0.05 was considered statistically significant. n=6 mice for each treatment group and is depicted by an asterisk.
Figure 11B:
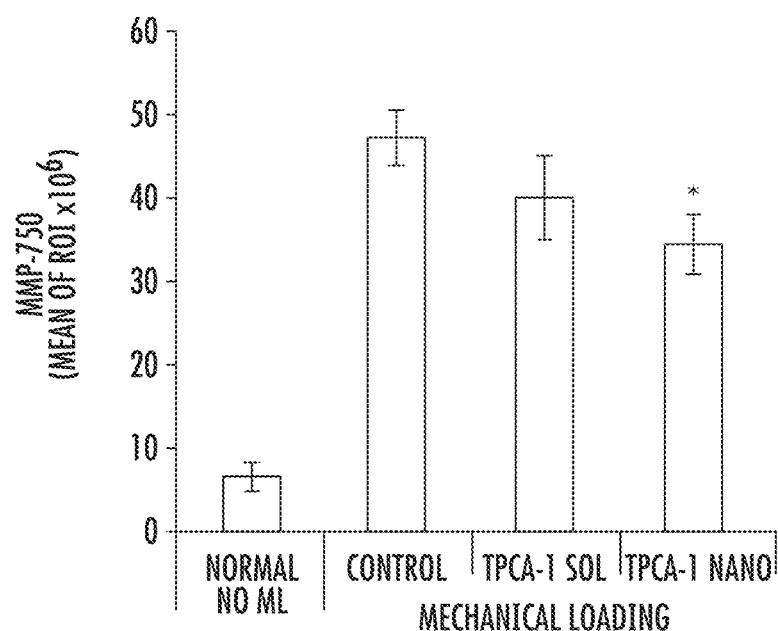

Quantitative measurement of the knee fluorescence showed that there were significant differences ($p<0.05$) in binding of MabCII680 in the knee and ankle of the loaded limb as measured by intensity in the region of interest (ROI) in the group treated with TPCA-1-loaded nanosomes as compared to the mechanically loaded knees treated with empty nanosomes (Control) (FIG. 11A). Soluble TPCA-1 did not show significant improvement ((FIG. 11A)). The results support that there was less damaged cartilage in the group treated with TPCA-1-loaded nanosomes than the group treated with control nanosomes or soluble TPCA-1 only. Scanning also revealed that there was lower intensity of fluorescence of MMPSense-750 ($p<0.05$) in the group treated with TPCA-1-loaded nanosomes than in the group treated with control nanosomes ((FIG. 11B). This result indicates that the group treated with targeted nanosomes had lower activity of MMPs than other groups.

DISCUSSION

A substantial body of evidence supports that the increased expression of MMP-13, a critical enzyme for OA development, occurs in PTOA is a result of activation of the NF-κB pathway [17, 23]. We hypothesized that by inhibiting IKK-2 and activation of this pathway with the drug TPCA-1, the amount of cartilage degradation and MMP activity that typically occurs in response to a noninvasive repetitive mechanical stress could be reduced. The results indicate that the IKK-2 inhibitor, TPCA-1, can significantly downregulate MMP expression and that reduction of MMP expression is protective of exposure of type II collagen at the articular surface even within the two-week loading interval. The correlative decrease in MMP activity and MabCII binding indicate that exposure of type II collagen at the articular surface is likely due to proteolytic activity of the MMP family that degrade many different substrates. The removal of the molecules at the surface of the articular cartilage could certainly contribute to an increased frictional component that would increase mechanical stress on the superficial chondrocytes. This could set in motion an irreversible spiraling decline with amplification of NF-κB activation and expression of its downstream target genes such as the transcription factor hypoxia induced factor 1 alpha and its target gene, MMP-13, so critical to OA development [23, 24].

The data further show that MabCII-targeted nanosomes are an effective vehicle for drug delivery. Although an equivalent amount of soluble TPCA-1 was injected systemically, the mice receiving this treatment did not show significant reduction in either MMP activity or exposure of type II collagen, thus indicating that rapid clearance or dilution of the soluble drug rendered it ineffective to a large degree. This supports that the localization of the targeted nanosomes loaded with TPCA-1 to the damaged cartilage delivered a more sustained delivery and/or relatively higher concentration of the drug. These data are greatly encouraging that local inhibition of the NF-κB pathway can be an effective strategy for reducing OA progression in patients with sports-related or traumatic injury. Since time of the evoking incident in these patients at risk can be identified, such an approach is feasible to clinically test.

The ability to use fluorescent theranostic nanosomes for both drug delivery and quantitative analyses of degradation of joint cartilages and the exposure of type II collagen without euthanasia allows quantitation of an initial baseline for individual animals and provides measurable outcomes that can be serially followed in the testing of therapeutic drugs in small animal models of OA. For OA, a disease of articular cartilage that has been shown to vary in the randomness of its presentation in the joints and the degree of severity in the same animal, theranostic nanosomes provide invaluable efficacy and outcome data and at the same time allow the maximum amount of drug to be locally delivered to the joints with the most disease in early stages of OA.

Example 3—Evaluation of Type II Collagen Antibody-Targeted Nanosomes (D1 2G Monoclonal Antibody)

This study is similar to that of Example 2, except that MabCII antibody D1 2G was used instead of E4.

Preparation of Targeted Nanosome (D1 2G)

Targeted nanosomes were generated from lipids and conjugated to purified D1 2G monoclonal antibody from a hybridoma isolated from mice immunized with type II collagen (MabCII). Briefly, the lipid film which contained 5.2 μmol dioleoyl-sn-glycero-3-phosphocholine (DOPC), 4.5 μmol cholesterol, 0.3 μmol 1,2-distearoyl-sn-glycero-3-phosphoethanolamine-N-[maleimide (polyethylene glycol) 2000] (DSPE-PEG-maleimide) and TPCA-1 was rehydrated with phosphate buffered saline (PBS) and sonicated. The rehydrated lipids were repeatedly extruded through a 200 nm porous membrane to generate 200 nm 1-3 walled nanosomes. The MabCII were thiolated using Traut's reagent, then mixed with the nanosomes for conjugation. After conjugation, the reaction mixture was chromatographed on a Sepharose CL-4B column to separate the free antibodies from the coupled liposomes.

Treatment

The C57BL/6 mice aged 10 weeks (n=18) were divided into three different treatment groups: PBS, TPCA-1 solution (500 μM) and TPCA-1-loaded, MabCII-targeted nanosomes (containing 500 uM of TPCA-1 per equivalent volume to the TPCA-1 solution). Each mouse received an intraarticular injection of 50 μL, of solution in the left knee joint 24 hours prior to exposure to mechanical loading. A group of mice that did not receive any treatment served as a normal non-loaded control. The treated groups received a second injection midway through the six mechanical loading episodes. The MabCII antibody-targeted nanosomes were also delivered by systemic injection (data not shown), with both types of administration resulting in localization to damaged cartilage in the joint.

Mechanical Loading to Induce OA

A loading episode of 40 cycles of 9 N compressive loading was given three times a week over a period of two weeks using conditions adapted from Poulet et al. (6). Mice of equivalent weight (<10% variance) were anesthetized with 2% isofluorane. The left leg of each mouse was positioned within a Bose ElectroForce 3200 electromagnetic testing system: the proximal tibia rested in the upper cup with the dorsiflexed ankle inserted into the bottom cup. The load was administered with a static offset load of 2 N used to maintain contact between the specimen and the load cell. All animal protocols were approved by the VA IACUC.

Analysis

At the completion of the two-week loading period, mice were injected retro-orbitally with 100 μL composite mixture of 50 μL of monoclonal antibody to type II collagen (MabCII680) labeled with XenoFluor 680 (XF680; Caliper) fluorescent dye and 50 μL of MMPSense-750 (Perkin-Elmer, Waltham, Mass.) a substrate that fluoresces when cleaved by MMPs. After 24 hours, the mice were anesthetized and the knee joints were optically scanned for each type of fluorescence using a Lumina XR (Perkin Elmer, Waltham, Mass.).

Results and Discussion

Optical scanning was used to visualize the systemic distribution of the MabCII680 in the mechanically loaded mouse knee. Briefly, MabCII labeled with the XF680 dye was not detectable in the knees of normal mice (data not shown). Measurable XF680 fluorescence was only seen in compressively loaded knees of mice injected with fluorescent MabCII while no fluorescence was detected in the contralateral knee of the same mouse (data not shown). This binding thus demonstrates specificity for the damaged cartilage in the loaded left knee as we have reported previously (7).

Quantitative measurement of the knee fluorescence showed that there were significant differences in binding of MabCII680 as measured by intensity in the region of interest (ROI) in the group treated with TPCA-1-loaded nanosomes as compared to the mechanically loaded knees treated with with PBS. Treatment with soluble TPCA-1 only showed no improvement (data not shown). The results indicate that there was less damaged cartilage in the group treated with TPCA-1-loaded nanosomes than the group treated with PBS or soluble TPCA-1 only. Scanning also revealed that there was lower intensity of fluorescence of MMPSense-750 in the group treated with TPCA-1-loaded nanosomes than in the group treated with PBS. This result indicates that the group treated with targeted nanosomes had lower expression of MMPs than other groups.

Example 4—Evaluation of Type II Collagen Antibody-Targeted Adipose Derived Stem Cells Treatment In Vivo in a Damaged Pig Knee (E4 Monoclonal Antibody)

In this example, which follows the method set for in FIG. 4A and FIG. 4B, fluorescent ADSC cells were linked to a complex of biotin, neutravidin and biotinylated MabCII antibody E4 before injection into the knee of a domestic pig, where the articular cartilage has been damaged by arthroscopic surgery.

Materials and Methods

Biotinylation of Monoclonal Antibodies to Type II Cartilage (E4 Clone)

Type II collagen monoclonal antibody (MabCII) at a concentration of 1 mg/mL was buffer exchanged with phosphate buffered saline (PBS). The linking reagent NHS- PEG12-Biotin (Thermo Scientific) was then brought up in distilled water to a recommended 20-fold molar excess of Biotin per mg/mL of MabCII. The biotinylated MabCII sample was then added to a Zeba spin desalting column (Thermo Scientific) column and centrifuged at 1000×g for 2 minutes in order to remove excess biotin reagent. The collected flow-through solution was the purified sample. As a control, irrelevant monoclonal mouse IgG antibody of the same subclass (Isotope Control from R&D Systems, Inc.) was similarly prepared.

Cell Labeling with PEG-Biotin, Neutravidin and MabCII

A stock solution of DSPE-PEG(2000) Biotin (1,2-distearoyl-sn-glycero-3-phosphoethanolamine-N-[biotinyl (polyethylene glycol)-2000] ammonium salt) (PE-PEG-Biotin; Avanti Polar Lipids, Inc) (10 mg/ml) was dried under nitrogen and then vacuumed dried for 15 minutes. The dried PE-PEG-Biotin was then brought up in 1.0 ml of a solution of 250 mM Sucrose and 1 mM HEPES, pH 7.2 to give a stock PE-PEG-Biotin solution of 35 uM. The solution was incubated for 5 minutes at 37° C., then sonicated for 5 minutes in a bath sonicator, and finally, was heated for 5 minutes in a water bath at 50° C.

The reparative cells (ADSCs) previously labeled with a fluorescent dye (Vivotrack 680: PerkinElmer, MA), were re-suspended at $2 \times 10^6$ cells/ml in the PE-PEG-Biotin stock solution and incubated for 10 minutes to allow PE-PEG-Biotin integration into the cell membranes, washed with serum free medium and incubated for an additional 20 minutes at 37° C. at $2 \times 10^6$ cells/ml in serum free medium. Neutravidin was dissolved in water at 20 mg/ml and 50 μl of Neutravidin/$2 \times 10^6$ cells was added. The cells were then allowed to incubate on a rocker platform for 30 minutes at 37° C. for binding of avidin. After incubation, the cells were washed and incubated for 60 minutes at 37° C. with 50 μg of biotinylated MabCII (clone E4)/$2 \times 10^6$ cells/ml in serum free medium. Cells are washed and counted before resuspension at $3.6 \times 10^6$ cell/ml in serum free medium for injection into the damaged pig knee.

Surgical Damage to Articular Cartilage in the Pig Knee.

Damage to the femoral cartilage in the knee of a domestic pig was created by curettage using arthroscopic surgery. A 79 lb female domestic pig was anesthetized and the femoral cartilage was physically traumatized with a curette using arthroscopy before closure of the knee and intra-articular injection of 2 ml of $7.2 \times 10^6$ fluorescent (Vivotrack 680: PerkinElmer, MA) reparative cells (ADSC) previously labeled at the cell surface with a biotin, Neutravidin and MabCII complex (See, e.g., FIG. 4B). The pig was allowed to recover and thereafter euthanized 48 hr after the surgical procedure. The treated knee was removed, opened, macroscopically observed and optically scanned using a Lumina II (Caliper Life Science, Hopkinton, Mass.) in vitro imaging system (IVIS) to visualize the localization of the fluorescent reparative cells.

Results and Discussion

Binding to Localized Cartilage Lesions

Figure 12C:
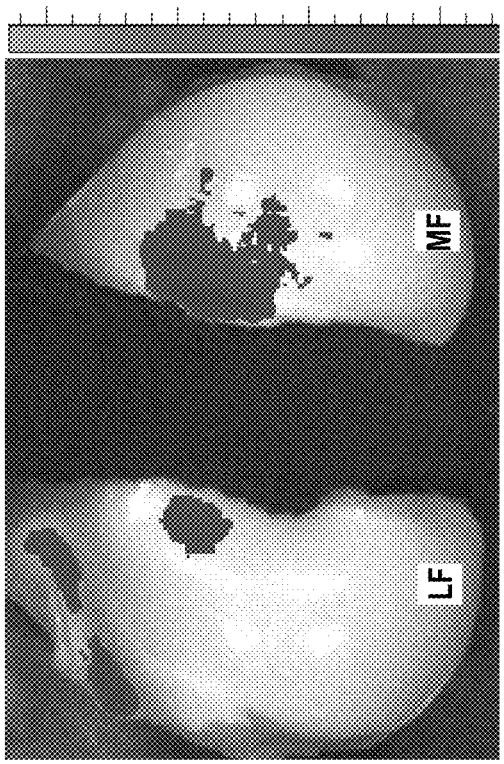
FIGS. 12A-12C are series of images of a pig knee that was surgically damaged and treated in vivo with an intra-articular injection of fluorescent E4 MabCII-targeted adipose-derived stem cells (ADSCs), in accordance with certain example embodiments. More particularly.
Figure 12A:
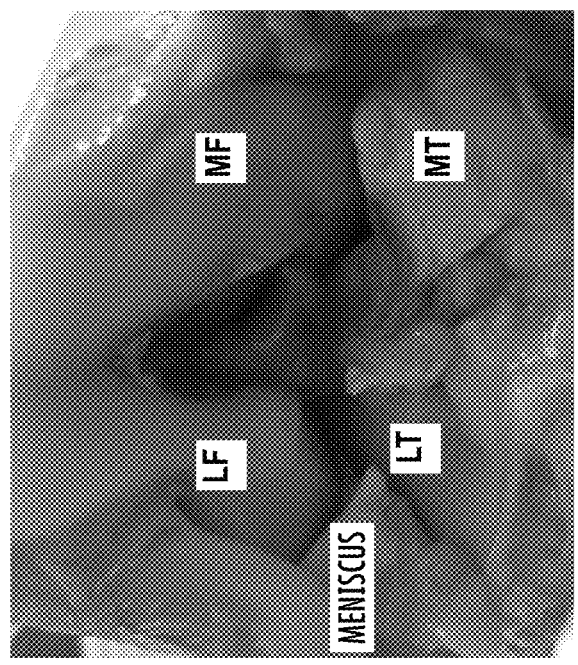
Figure 12B:
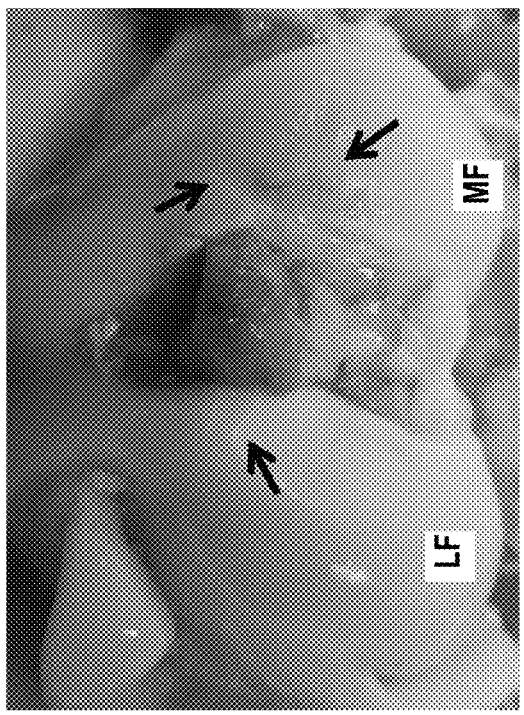

The gross morphology of the treated pig knee (FIG. 12A) is shown for the cartilages of the medial femoral (MF), lateral femoral (LF), medial tibial (MT) and the lateral tibial (LT) condyles and meniscal cartilage showed no sign of infection. Upon dissection and removal of the femoral condyles, closer examination (FIG. 12B) reveals distinct abrasions on the cartilage of the medial femoral (MF) and the lateral femoral (LF) condyles. As shown in FIG. 12C, IVIS imaging of the dissected femoral condyles shows fluorescent avidin/biotinylated ADSC cells bound (shading) to these abraded areas, but not to the surface of the normal cartilage although some cells were present in the soft tissue (upper left adjacent to the LF) at possibly the injection track. These data thus indicate that targeting of reparative cells with a monoclonal antibody to type II collagen can be used as a method for directing these cells in vivo to damaged articular cartilages in the surgically traumatized domestic pig knee.

REFERENCES

Each of the following references, including those referenced throughout the description above, are hereby expressly incorporated herein in their entirety.

1. Buckwalter J A, Mankin H J. Articular cartilage. 2: Degeneration and osteoarthrosis, repair, regeneration, and transplantation. J Bone Joint Surg. 1997; 79A: 612-632.
2. Silver F H, Bradica G, Tria A. Relationship among biomechanical, biochemical and cellular changes associated with osteoarthritis. Crit Rev Biomed Eng. 2001; 29(4):373-391.
3. Sandell L J, Aigner T. Articular cartilage and changes in arthritis. An introduction: Cell biology of osteoarthritis. Arthritis Research and Therapy. 2001; 3: 107-113.
4. Hollander A P, Pidoux I, Reiner A, Rorabeck C, Bourne R, Poole R. Damage to type II collagen in aging and osteoarthritis starts at the articular surface, originates around chondrocytes, and extends into the cartilage with progressive degeneration. J. Clinical Investigation. 1995; 96: 2859-2869.
5. Jasin H E, Noyori K, Takagi T, Taurog J D. Characteristics of anti-type II collagen antibody binding to articular cartilage. Arthritis Rheum. 1993; 36(5): 651-659.
6. Noyori K, Koshino T, Takagi T, Okamoto R, Jasin H E. Binding characteristics of antitype II collagen antibody to the surface of diseased human cartilage as a probe for tissue damage. J. Rheum. 1994; 21(2): 293-296.
7. Cho H, Stuart J M, Magid R, Danila D C, Hunsaker T, Pinkhassik E, Hasty K A. Theranostic Immunoliposomes for Osteoarthritis. Nanomedicine: NBM. 2014; 10(3): 619-627.
8. Cho H, Pinkhassik E, David V, Stuart J M, Hasty K A. "Detection of Early Cartilage Damage using Targeted Nanosomes in a Post-Traumatic Osteoarthritis Mouse Model" Nanomedicine: NBM 2015; 11: 939-946.
9. Veronesi F, Maglio M, Tschon M, Aldini N N, Fini M. Adipose-derived mesenchymal stem cells for cartilage tissue engineering: State-of-the-art in in vivo studies J Biomed Mater Res A. 2014 July; 102(7):2448-2466.
10. Prockop D J. Repair of tissues by adult stem/progenitor cells (MSCs): controversies, myths, and changing paradigms. Molecular Therapy. 2009; 17(6):939-946.
11. Woods A, Chen H Y, Trumbauer M E, Sirotina A, Cummings R, Zaller D M. Human major histocompatibility complex class II-restricted T cell responses in transgenic mice. J. Exp. Med. 1994; 180:173-181.
12. Miller E J. Isolation and characterization of a collagen from chick cartilage containing three identical α-chains. Biochemistry 1971; 10:1652-1659.
13. Rosloniec E F, Brand D D, Myers L K, Esaki Y, Whittington K B, Zaller D M, Woods A, Stuart J M, Kang A H: Induction of autoimmune arthritis in HLA-DR4 (DRB1*0401) transgenic mice by immunization with human and bovine type II collagen. J. Immunol. 1998, 160:2573-2578.
14. Stuart J M, Cremer M A, Townes A S, Kang A H. Type II collagen induced arthritis in rats: passive transfer with serum and evidence that IgG anticollagen antibodies can cause arthritis. J. Exp. Med. 1982; 155: 1-16.
15. Hasty D L, Beachey E H, Simpson W A, Dale J B. Hybridoma antibodies against protective and nonprotective antigenic determinants of a structurally defined polypeptide fragment of streptococcal M protein. J. Exp. Med. 1982; 155:1010-1018.
16. Agarwal S, Deschner J, Long P, Verma A, Hofman C, Evans C H, Piesco N. Role of NF-kappaB transcription factors in antiinflammatory and proinflammatory actions of mechanical signals. Arthritis Rheum. 2004 November; 50(11):3541-8. PubMed PMID: 15529376.
17. Marcu K B, Otero M, Olivotto E, Borzi R M, Goldring M B. NF-kappaB signaling: multiple angles to target OA. Curr Drug Targets. 2010 May; 11(5):599-613. Review. PubMed PMID: 20199390; PubMed Central PMCID: PMC3076145.
18. Mengshol J A, Vincenti M P, Coon C I, Barchowsky A, Brinckerhoff C E. Interleukin-1 induction of collagenase 3 (matrix metalloproteinase 13) gene expression in chondrocytes requires p38, c-Jun N-terminal kinase, and nuclear factor kappaB: differential regulation of collagenase 1 and collagenase 3. Arthritis Rheum. 2000 April; 43(4):801-11. PubMed PMID: 10765924.
19. Zandi E, Rothwarf D M, Delhase M, Hayakawa M, Karin M. The IkappaB kinase complex (IKK) contains two kinase subunits, IKKalpha and IKKbeta, necessary for IkappaB phosphorylation and NF-kappaB activation. Cell. 1997 Oct. 17; 91(2):243-52. PubMed PMID: 9346241.
20. Podolin P L, Callahan J F, Bolognese B J, Li Y H, Carlson K, Davis T G, Mellor G W, Evans C, Roshak A K. Attenuation of murine collagen-induced arthritis by a novel, potent, selective small molecule inhibitor of IkappaB Kinase 2, TPCA-1 (2-[(aminocarbonyl)amino]-5-(4-fluorophenyl)-3-thiophenecarboxamide), occurs via reduction of proinflammatory cytokines and antigen-induced T cell Proliferation. J Pharmacol Exp Ther. 2005 January; 312(1):373-81. Epub 2004 Aug. 17. PubMed PMID: 15316093.
21. Poulet B, Hamilton R W, Shefelbine S, Pitsillides A A. Characterizing a novel and adjustable noninvasive murine joint loading model. Arthritis Rheum. 2011 January; 63(1):137-47. doi: 10.1002/art.27765. PubMed PMID: 20882669.
22. Cho H, Pinkhassik E, David V, Stuart J M, Hasty K A. Detection of early cartilage damage using targeted nanosomes in a post-traumatic osteoarthritis mouse model. Nanomedicine. 2015 May; 11(4):939-46. doi: 10.1016/j.nano.2015.01.011. Epub 2015 Feb. 11. PubMed PMID: 25680539.
23. Saito T, Fukai A, Mabuchi A, Ikeda T, Yano F, Ohba S, Nishida N, Akune T, Yoshimura N, Nakagawa T, Nakamura K, Tokunaga K, Chung U I, Kawaguchi H. Transcriptional regulation of endochondral ossification by HIF-2alpha during skeletal growth and osteoarthritis development. Nat Med. 2010 June; 16(6):678-86. doi: 10.1038/nm.2146. Epub 2010 May 23. PubMed PMID: 20495570.
24. Wang M, Sampson E R, Jin H, Li J, Ke Q H, Im H J, Chen D. MMP13 is a critical target gene during the progression of osteoarthritis. Arthritis Res Ther. 2013 Jan. 8; 15(1): R5. doi: 10.1186/ar4133.

We claim:

1. A method of targeting nanosomes to a cartilage lesion in a subject, comprising:

chemically linking an antibody or antigen-binding fragment thereof to a nanosome, wherein the antibody or antigen-binding fragment thereof binds type II collagen and comprises the heavy and light chain CDRs of a variable heavy/variable light (VH/VL,) amino acid sequence pair set forth as SEQ) ID NO: 6/14; and administering the nanosome that is linked to the antibody or antigen-binding fragment thereof to a subject, wherein the administration occurs at a cartilage lesion in the subject.

2. The method of claim 1, wherein administering the nanosome that is linked to the antibody or antigen-binding fragment thereof results in binding of the nanosome to an epitope at the cartilage lesion via the antibody-epitope linkage.

3. The method of claim 1, wherein the nanosome encapsulates a pharmaceutical agent.

4. The method of claim 3, wherein the pharmaceutical agent is an NF-κB inhibitor.

5. The method of claim 3, wherein the pharmaceutical agent is 2-aminocarbonyl)aminol-5-(4-fluorophenyl)-3thiophenecarboxamide (TPCA-1A.

6. The method of claim 3, wherein lysis of the nanosome at the cartilage lesion exposes the lesion to the pharmaceutical agent.

7. The method of claim 1, wherein the antibody or antigen-binding fragment comprises HCDR1-HCDR2-HCDR3-LCDR1-LCDR2-LCDR3 domains set forth as SEQ ID NOs:8-10-12-16-18-20.

8. An isolated antibody or antigen-binding fragment thereof that binds type II collagen, wherein the antibody or antigen-binding fragment comprises the heavy and light chain CDRs of a VH/VL amino acid sequence pair set forth as SEQ ID NO: 6/14.

9. The isolated antibody or antigen-binding fragment of claim 8, wherein the antibody or antigen-binding fragment comprises HCDR1-HCDR2-HCDR3-LCDR1-LCDR2-LCDR3 domains set forth as SEQ ID NOs:8-10-12-16-18-20.

10. The isolated antibody or antigen-fragment thereof of claim 8, further labeled with biotin.

* * * * *

SEQUENCE LISTING

```
<160> NUMBER OF SEQ ID NOS: 20

<210> SEQ ID NO 1
<211> LENGTH: 448
<212> TYPE: PRT
<213> ORGANISM: Mus musculus

<400> SEQUENCE: 1

Glu Val Gln Leu Val Glu Ser Gly Gly Gly Leu Val Lys Pro Gly Gly
1               5                   10                  15

Ser Leu Lys Val Ser Cys Glu Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Val Ser Ser Thr Ile Tyr Ala Asp Thr Val
    50                  55                  60

Glu Gly Arg Phe Thr Ile Ser Arg Asp Asn Val Arg Asn Thr Leu Phe
65                  70                  75                  80

Leu Gln Met Thr Ser Leu Arg Ser Glu Asp Thr Ala Met Tyr Tyr Cys
                85                  90                  95

Ala Arg Glu Gly Trp Leu Pro Leu Phe Ala Phe Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
```

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Ser Gly Ser Leu Ser Ser Gly Val His Thr Phe Pro Ala Val Leu Gln
                165                170                175

Ser Asp Leu Tyr Thr Leu Ser Ser Val Thr Val Thr Ser Ser Thr
                180                185                190

Trp Pro Ser Gln Ser Ile Thr Cys Asn Val Ala His Pro Ala Ser Ser
                195                200                205

Thr Lys Val Asp Lys Lys Ile Glu Pro Arg Gly Pro Thr Ile Lys Pro
210                        215                    220

Cys Pro Pro Cys Lys Cys Pro Ala Pro Asn Leu Leu Gly Gly Pro Ser
225                        230                235                240

Val Phe Ile Phe Pro Pro Lys Ile Lys Asp Val Leu Met Ile Ser Leu
                245                250                255

Ser Pro Ile Val Thr Cys Val Val Asp Val Ser Glu Asp Pro
                260                265                270

Asp Val Gln Ile Ser Trp Phe Val Asn Asn Val Glu Val His Thr Ala
                275                280                285

Gln Thr Gln Thr His Arg Glu Asp Tyr Asn Ser Thr Leu Arg Val Val
        290                295                300

Ser Ala Leu Pro Ile Gln His Gln Asp Trp Met Ser Gly Lys Glu Phe
305                        310                315                320

Lys Cys Lys Val Asn Asn Lys Asp Leu Pro Ala Pro Ile Glu Arg Thr
                325                330                335

Ile Ser Lys Pro Lys Gly Ser Val Arg Ala Pro Gln Val Tyr Val Leu
                340                345                350

Pro Pro Pro Glu Glu Glu Met Thr Lys Lys Gln Val Thr Leu Thr Cys
        355                360                365

Met Val Thr Asp Phe Met Pro Glu Asp Ile Tyr Val Glu Trp Thr Asn
        370                375                380

Asn Gly Lys Thr Glu Leu Asn Tyr Lys Asn Thr Glu Pro Val Leu Asp
385                        390                395                400

Ser Asp Gly Ser Tyr Phe Met Tyr Ser Lys Leu Arg Val Glu Lys Lys
                405                410                415

Asn Trp Val Glu Arg Asn Ser Tyr Ser Cys Ser Val Val His Glu Gly
                420                425                430

Leu His Asn His His Thr Thr Lys Ser Phe Ser Arg Thr Pro Gly Lys
                435                440              445

```
<210> SEQ ID NO 2
<211> LENGTH: 234
<212> TYPE: PRT
<213> ORGANISM: Mus musculus

<400> SEQUENCE: 2
```

Met Glu Ser Gln Ser Leu Val Phe Val Phe Val Phe Leu Trp Leu Ser
1               5                    10                15

Gly Val Asp Gly Asp Ile Val Leu Thr Gln Ser His Lys Phe Met Ser
                20                25                30

Thr Ser Val Gly Asp Arg Val Ser Ile Thr Cys Lys Ala Ser Gln Asp
                35                40                45

Val Ser Ile Thr Val Ala Trp Tyr Gln Gln Lys Pro Gly Gln Ser Pro
        50                55                60

Lys Leu Leu Ile Tyr Ser Ala Ser Tyr Arg Asn Pro Gly Val Pro Asp
65                        70                75                80

```
Arg Phe Thr Gly Ser Gly Ser Gly Thr Asp Phe Asn Phe Thr Ile Ser
                85                  90                  95
Thr Val Gln Ala Glu Asp Leu Ala Val Tyr Tyr Cys Gln Gln Tyr Tyr
            100                 105                 110
Ile Ile Pro Trp Thr Phe Gly Gly Gly Thr Lys Leu Glu Phe Lys Arg
        115                 120                 125
Ala Asp Ala Ala Pro Thr Val Ser Ile Phe Pro Pro Ser Ser Glu Gln
    130                 135                 140
Leu Thr Ser Gly Gly Ala Ser Val Val Cys Phe Leu Asn Asn Phe Tyr
145                 150                 155                 160
Pro Lys Asp Ile Asn Val Lys Trp Lys Ile Asp Gly Ser Glu Arg Gln
                165                 170                 175
Asn Gly Val Leu Asn Ser Trp Thr Asp Gln Asp Ser Lys Asp Ser Thr
            180                 185                 190
Tyr Ser Met Ser Ser Thr Leu Thr Leu Thr Lys Asp Glu Tyr Glu Arg
        195                 200                 205
His Asn Ser Tyr Thr Cys Glu Ala Thr His Lys Thr Ser Thr Ser Pro
    210                 215                 220
Ile Val Lys Ser Phe Asn Arg Asn Glu Cys
225                 230
```

<210> SEQ ID NO 3
<211> LENGTH: 1344
<212> TYPE: DNA
<213> ORGANISM: Mus musculus

<400> SEQUENCE: 3

```
gaggtgcagc tggtggagtc tgggggaggc ttagtgaagc ctggagggtc cctgaaagtc      60
tcctgtgaag cctctggatt cactttcagt gactatggaa tgcactgggt cgtcaggct     120
ccagagaagg gactggagtg ggttgcatac atcagtagtg tcagtagtac catctactat     180
gcagacacag tggagggccg attcaccatc tccagagaca atgtcaggaa cacccctgttc    240
ctgcaaatga ccagtctgag gtctgaggac acggccatgt attactgtgc aagggaggga     300
tggttgcccc tgtttgcttt ctggggccaa gggactctgg tcactgtctc tgcagccaaa     360
acaacagccc catcggtcta tccactggcc ctgtgtgtg gagatacaac tggctcctcg     420
gtgactctag gatgcctggt caagggttat tccctgagc cagtgacctt gacctggaac     480
tctggatccc tgtccagtgg tgtgcacacc ttcccagctg tcctgcagtc tgacctctac     540
accctcagca gctcagtgac tgtaacctcg agcacctggc ccagccagtc catcacctgc     600
aatgtggccc accggcaag cagcaccaag gtggacaaga aaattgagcc cagagggccc     660
acaatcaagc cctgtcctcc atgcaaatgc ccagcaccta acctcttggg tggaccatcc     720
gtcttcatct tccctccaaa gatcaaggat gtactcatga tctccctgag ccccatagtc     780
acatgtgtgg tggtggatgt gagcgaggat gacccagatg tccagatcag ctggtttgtg     840
aacaacgtgg aagtacacac agctcagaca caaacccata gagaggatta caacagtact     900
ctccgggtgg tcagtgccct ccccatccag caccaggact ggatgagtgg caaggagttc     960
aaatgcaagg tcaacaacaa agacctccca gcgcccatcg agaaccat ctcaaaaccc     1020
aaagggtcag taagagctcc acaggtatat gtcttgcctc caccagaaga agagatgact     1080
aagaaacagg tcactctgac ctgcatggtc acagacttca tgcctgaaga catttacgtg     1140
gagtggacca acaacgggaa aacagagcta aactacaaga cactgaacc agtcctggac     1200
tctgatggtt cttacttcat gtacagcaag ctgagagtgg aaaagaagaa ctgggtggaa     1260
```

| | | | |
|---|---|---|---|
| agaaatagct actcctgttc agtggtccac gagggtctgc acaatcacca cacgactaag | | | 1320 |
| agcttctccc ggactccggg taaa | | | 1344 |

<210> SEQ ID NO 4
<211> LENGTH: 702
<212> TYPE: DNA
<213> ORGANISM: Mus musculus

<400> SEQUENCE: 4

| | |
|---|---|
| atggagtcac agtccctggt ctttgtattc gtgtttctct ggttgtctgg tgttgacgga | 60 |
| gacattgtgt tgacccagtc tcacaaattc atgtccacat cagttggaga cagggtcagc | 120 |
| atcacctgca aggccagtca ggatgtgagt attactgtag cctggtatca acagaaacca | 180 |
| ggacaatctc ctaaactact gatttactcg gcatcctacc ggaaccctgg agtcccagat | 240 |
| cgcttcactg gcagtggatc tgggacggat ttcaatttca ccatcagcac tgtgcaggct | 300 |
| gaggacctgg cagtttatta ctgtcagcaa tattatatta ttccgtggac gttcggtgga | 360 |
| ggcaccaagc tggaattcaa acgggctgat gctgcaccaa ctgtatccat cttcccacca | 420 |
| tccagtgagc agttaacatc tggaggtgcc tcagtcgtgt gcttcttgaa caacttctac | 480 |
| cccaaagaca tcaatgtcaa gtggaagatt gatggcagtg aacgacaaaa tggcgtcctg | 540 |
| aacagttgga ctgatcagga cagcaaagac agcacctaca gcatgagcag cacccctcacg | 600 |
| ttgaccaagg acgagtatga acgacataac agctatacct gtgaggccac ccacaagaca | 660 |
| tcaacttcac ccattgtcaa gagcttcaac aggaatgagt gt | 702 |

<210> SEQ ID NO 5
<211> LENGTH: 354
<212> TYPE: DNA
<213> ORGANISM: Mus musculus

<400> SEQUENCE: 5

| | |
|---|---|
| gaggtgcagc tggtggagtc tgggggaggc ttagtgaagc ctggagggtc cctgaaagtc | 60 |
| tcctgtgaag cctctggatt cactttcagt gactatggaa tgcactgggt tcgtcaggct | 120 |
| ccagagaagg gactggagtg ggttgcatac atcagtagtg tcagtagtac catctactat | 180 |
| gcagacacag tggagggccg attcaccatc tccagagaca atgtcaggaa caccctgttc | 240 |
| ctgcaaatga ccagtctgag gtctgaggac acggccatgt attactgtgc aagggaggga | 300 |
| tggttgcccc tgtttgcttt ctggggccaa gggactctgg tcactgtctc tgca | 354 |

<210> SEQ ID NO 6
<211> LENGTH: 118
<212> TYPE: PRT
<213> ORGANISM: Mus musculus

<400> SEQUENCE: 6

Glu Val Gln Leu Val Glu Ser Gly Gly Gly Leu Val Lys Pro Gly Gly
1               5                   10                  15

Ser Leu Lys Val Ser Cys Glu Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Val Ser Ser Thr Ile Tyr Tyr Ala Asp Thr Val
    50                  55                  60

Glu Gly Arg Phe Thr Ile Ser Arg Asp Asn Val Arg Asn Thr Leu Phe
65                  70                  75                  80

Leu Gln Met Thr Ser Leu Arg Ser Glu Asp Thr Ala Met Tyr Tyr Cys
            85                  90                  95

Ala Arg Glu Gly Trp Leu Pro Leu Phe Ala Phe Trp Gly Gln Gly Thr
        100                 105                 110

Leu Val Thr Val Ser Ala
        115

<210> SEQ ID NO 7
<211> LENGTH: 21
<212> TYPE: DNA
<213> ORGANISM: Mus musculus

<400> SEQUENCE: 7
ggattcactt tcagtgacta t                                         21

<210> SEQ ID NO 8
<211> LENGTH: 7
<212> TYPE: PRT
<213> ORGANISM: Mus musculus

<400> SEQUENCE: 8

Gly Phe Thr Phe Ser Asp Tyr
1               5

<210> SEQ ID NO 9
<211> LENGTH: 18
<212> TYPE: DNA
<213> ORGANISM: Mus musculus

<400> SEQUENCE: 9
agtagtgtca gtagtacc                                             18

<210> SEQ ID NO 10
<211> LENGTH: 6
<212> TYPE: PRT
<213> ORGANISM: Mus musculus

<400> SEQUENCE: 10

Ser Ser Val Ser Ser Thr
1               5

<210> SEQ ID NO 11
<211> LENGTH: 27
<212> TYPE: DNA
<213> ORGANISM: Mus musculus

<400> SEQUENCE: 11
gagggatggt tgcccctgtt tgctttc                                   27

<210> SEQ ID NO 12
<211> LENGTH: 9
<212> TYPE: PRT
<213> ORGANISM: Mus musculus

<400> SEQUENCE: 12

Glu Gly Trp Leu Pro Leu Phe Ala Phe
1               5

<210> SEQ ID NO 13
<211> LENGTH: 324
<212> TYPE: DNA
<213> ORGANISM: Mus musculus

<400> SEQUENCE: 13

```
gacattgtgt tgacccagtc tcacaaattc atgtccacat cagttggaga cagggtcagc    60
atcacctgca aggccagtca ggatgtgagt attactgtag cctggtatca acagaaacca   120
ggacaatctc ctaaactact gatttactcg gcatcctacc ggaacccctgg agtcccagat  180
cgcttcactg gcagtggatc tgggacggat ttcaatttca ccatcagcac tgtgcaggct   240
gaggacctgg cagtttatta ctgtcagcaa tattatatta ttccgtggac gttcggtgga   300
ggcaccaagc tggaattcaa acgg                                          324
```

<210> SEQ ID NO 14
<211> LENGTH: 108
<212> TYPE: PRT
<213> ORGANISM: Mus musculus

<400> SEQUENCE: 14

Asp Ile Val Leu Thr Gln Ser His Lys Phe Met Ser Thr Ser Val Gly
1               5                   10                  15
Asp Arg Val Ser Ile Thr Cys Lys Ala Ser Gln Asp Val Ser Ile Thr
            20                  25                  30
Val Ala Trp Tyr Gln Gln Lys Pro Gly Gln Ser Pro Lys Leu Leu Ile
        35                  40                  45
Tyr Ser Ala Ser Tyr Arg Asn Pro Gly Val Pro Asp Arg Phe Thr Gly
    50                  55                  60
Ser Gly Ser Gly Thr Asp Phe Asn Phe Thr Ile Ser Thr Val Gln Ala
65                  70                  75                  80
Glu Asp Leu Ala Val Tyr Tyr Cys Gln Gln Tyr Tyr Ile Ile Pro Trp
                85                  90                  95
Thr Phe Gly Gly Gly Thr Lys Leu Glu Phe Lys Arg
            100                 105

<210> SEQ ID NO 15
<211> LENGTH: 33
<212> TYPE: DNA
<213> ORGANISM: Mus musculus

<400> SEQUENCE: 15

```
aggaccagtc aggatgtgag tattactgta gcc                                 33
```

<210> SEQ ID NO 16
<211> LENGTH: 11
<212> TYPE: PRT
<213> ORGANISM: Mus musculus

<400> SEQUENCE: 16

Lys Ala Ser Gln Asp Val Ser Ile Thr Val Ala
1               5                   10

<210> SEQ ID NO 17
<211> LENGTH: 21
<212> TYPE: DNA
<213> ORGANISM: Mus musculus

<400> SEQUENCE: 17

```
tcggcatcct accggaaccc t                                              21
```

<210> SEQ ID NO 18
<211> LENGTH: 7
<212> TYPE: PRT
<213> ORGANISM: Mus musculus

```
<400> SEQUENCE: 18

Ser Ala Ser Tyr Arg Asn Pro
1               5

<210> SEQ ID NO 19
<211> LENGTH: 27
<212> TYPE: DNA
<213> ORGANISM: Mus musculus

<400> SEQUENCE: 19
cagcaatatt atattattcc gtggacg                                          27

<210> SEQ ID NO 20
<211> LENGTH: 9
<212> TYPE: PRT
<213> ORGANISM: Mus musculus

<400> SEQUENCE: 20

Gln Gln Tyr Tyr Ile Ile Pro Trp Thr
1               5
```